(12) United States Patent
Starr et al.

(10) Patent No.: US 9,295,838 B2
(45) Date of Patent: Mar. 29, 2016

(54) METHODS AND SYSTEMS FOR TREATING NEUROLOGICAL MOVEMENT DISORDERS

(71) Applicants: The Regents of the University of California, Oakland, CA (US); U.S. Government—Department of Veterans Affairs, Washington, DC (US)

(72) Inventors: Philip A. Starr, Mill Valley, CA (US); Coralie de Hemptinne, San Francisco, CA (US); Jill Ostrem, Greenbrae, CA (US); Nicole Swann, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 36 days.

(21) Appl. No.: 14/069,170

(22) Filed: Oct. 31, 2013

(65) Prior Publication Data
US 2014/0163627 A1 Jun. 12, 2014

Related U.S. Application Data

(60) Provisional application No. 61/720,876, filed on Oct. 31, 2012.

(51) Int. Cl.
*A61N 1/36* (2006.01)
*A61M 5/172* (2006.01)

(52) U.S. Cl.
CPC ......... *A61N 1/36067* (2013.01); *A61M 5/1723* (2013.01); *A61N 1/36139* (2013.01)

(58) Field of Classification Search
CPC ........... A61N 1/36067; A61N 1/36085; A61N 1/36096; A61N 1/36071; A61N 1/36075; A61N 1/36082
See application file for complete search history.

(56) References Cited

U.S. PATENT DOCUMENTS

| | | | |
|---|---|---|---|
| 5,716,377 A | 2/1998 | Rise et al. | |
| 5,843,148 A | 12/1998 | Gijsbers et al. | |
| 6,066,163 A | 5/2000 | John | |
| 6,227,203 B1 * | 5/2001 | Rise et al. | 607/46 |
| 6,253,109 B1 | 6/2001 | Gielen | |
| 6,463,328 B1 | 10/2002 | John | |
| 6,484,059 B2 | 11/2002 | Gielen | |
| 6,539,263 B1 | 3/2003 | Schiff et al. | |
| 6,587,724 B2 | 7/2003 | Mann | |
| 6,920,359 B2 | 7/2005 | Meadows et al. | |

(Continued)

OTHER PUBLICATIONS

Canolty et al., "High Gamma Power Is Phase-Locked to Theta Oscillations in Human Neocortex" Science, 2006, vol. 313, pp. 1626-1628.

(Continued)

*Primary Examiner* — George Evanisko
(74) *Attorney, Agent, or Firm* — Edward J. Baba; Shweta Chandra; Bozicevic, Field & Francis LLP

(57) ABSTRACT

The present disclosure provides methods for reducing the clinical presentations of a neurological movement disorder in a subject. Aspects of the methods include measuring cortical local field potentials (LFPs) from the subject's brain, calculating a modulation index related to brain synchronization from the LFPs, and administering deep brain stimulation to the subject if the calculated modulation index is outside of a threshold range. Also provided are devices, systems, and kits that may be used in practicing the subject methods.

36 Claims, 23 Drawing Sheets

(56) References Cited

U.S. PATENT DOCUMENTS

| | | | |
|---|---|---|---|
| 7,003,352 | B1 | 2/2006 | Whitehurst |
| 7,033,326 | B1 | 4/2006 | Pianca et al. |
| 7,149,574 | B2 | 12/2006 | Yun et al. |
| 7,151,961 | B1 | 12/2006 | Whitehurst et al. |
| 7,212,867 | B2 | 5/2007 | Van Venrooij et al. |
| 7,295,880 | B2 | 11/2007 | Gielen |
| 7,346,382 | B2 | 3/2008 | McIntyre et al. |
| 7,369,899 | B2 | 5/2008 | Malinowski et al. |
| 7,539,543 | B2 | 5/2009 | Schiff et al. |
| 7,809,446 | B2 | 10/2010 | Meadows |
| 7,904,134 | B2 | 3/2011 | McIntyre et al. |
| 7,957,808 | B2 | 6/2011 | Dawant et al. |
| 2008/0045775 | A1* | 2/2008 | Lozano .......................... 600/12 |
| 2009/0018609 | A1* | 1/2009 | DiLorenzo ...................... 607/45 |
| 2009/0082829 | A1* | 3/2009 | Panken et al. .................. 607/45 |
| 2009/0099627 | A1* | 4/2009 | Molnar et al. .................. 607/62 |

OTHER PUBLICATIONS

Cohen, "Assessing Transient Cross-Frequency Coupling in EEG Data" J Neurosci Methods, 2008, vol. 168, No. 2, pp. 494-499.

Crone et al., "Functional mapping of human sensorimotor cortex with electroencephalographic analysis II. Event related synchronization in the gamma band" Brain, 1998, vol. 121, pp. 2301-2315.

Crowell et al., "Oscillations in sensorimotor cortex in movement disorders: an electrocorticography study" Brain, 2012, vol. 135, pp. 615-630.

Hermes et al., "Automated electrocorticographic electrode localization on individually rendered brain surfaces" J Neurosci Methods, 2010, vol. 185, No. 2, pp. 293-298.

Miller et al., "Decoupling the Cortical Power Spectrum Reveals Real-Time Representation of Individual Finger Movements in Humans," J Neurosci, 2009, vol. 29, No. 10, pp. 3132-3137.

Miller et al., "Dynamic modulation of local population activity by rhythm phase in human occipital cortex during a visual search task," Frontiers in Human Neuroscience, 2010, vol. 4, Article 197, pp. 1-16.

Miller et al., "Human motor cortical activity is selectively phase-entrained on underlying rhythms" PLoS Comput Biol, 2012, 8(9):e1002655, pp. 1-21.

Ostrem et al., "Subthalamic nucleus deep brain stimulation in primary cervical dystonia" Neurology, 2011, vol. 76, pp. 870-878.

Penny et al., "Testing for nested oscillation" J. Neurosci. Methods, 2008, vol. 174, No. 1, pp. 50-61.

Shahlaie et al., "Intraoperative computed tomography for deep brain stimulation surgery: technique and accuracy assessment" Neurosurgery, 2011, vol. 68, pp. 114-124.

Starr et al., "Implantation of deep brain stimulators into the subthalamic nucleus: technical approach and magnetic resonance imaging—verified lead locations" Journal of Neurosurgery, 2002, vol. 97, pp. 370-387.

Tort et al., "Dynamic cross-frequency couplings of local field potential oscillations in rat striatum and hippocampus during performance of a T-maze task" Proc Natl Acad Sci USA, 2008, vol. 105, pp. 20517-20522.

Whitmer et al., "High frequency deep brain stimulation attenuates subthalamic and cortical rhythms in Parkinson's disease" Front. Hum. Neurosci, 2012, vol. 6, Article 155, pp. 1-18.

Yousry et al., "Localization of the motor hand area to a knob on the precentral gyrus" Brain, 1997, vol. 120, pp. 141-157.

* cited by examiner

A.

|  | Modulation index M1phase-M1amp (Means ± SEM) | Modulation index STNphase-M1amp (Means ± SEM) | p-value for difference |
|---|---|---|---|
| MI mean | 16.7±12.9 | 3.4±2.7 | P=0.002 |
| MI max | 48.6±29.1 | 15.5±9.7 | P=0.001 |
| Fmax phase (Hz) | 23.1±5.5 | 20.2±8.4 | P=0.26 |
| Fmax amp (Hz) | 95.2±41.1 | 98.4±49.9 | P=0.82 |
| Pref phase (radians) | -3.1±1.1 | 0.3±1.4 | P=0.58 |

FIG. 23

| Pts | age | ecog side | UPDRS III ON | UPDRS III OFF | Stimulation parameters | Score intra-op Before DBS | Score intra-op during DBS | Score intra-op after DBS |
|---|---|---|---|---|---|---|---|---|
| PD3 | 54 | L | 23 | 42 | 1-2+ 155 Hz 4V 60 μs | rigidity = 2 tremor = 0 | rigidity = 0 tremor = 0 | rigidity = 2 tremor = 1 |
| PD4 | 60 | R | 11 | 34 | 1-2+ 165 Hz 4V 60 μs | rigidity = 1 tremor = 1 | rigidity = 0 tremor = 0 | rigidity = 1 tremor = 0 |
| PD5 | 54 | L | 9 | 21 | 0-2+ 186 Hz 4V 60 μs | rigidity = NA tremor = 2 | rigidity = NA tremor = 1 | rigidity = NA tremor = NA |
| PD6 | 68 | R | 30 | 50 | 1-2+ 170 Hz 4V 60 μs | rigidity = 1 tremor = 1 | rigidity = 0 tremor = 0 | rigidity = 2 tremor = 1 |
| PD8 | 63 | R | 12 | 40 | 1-2+ 213 Hz 4V 60 μs | rigidity = 1 tremor = 0 | rigidity = 0 tremor = 0 | rigidity = NA tremor = NA |
| PD9 | 58 | L | 31 | 52 | 1-2+ 179 Hz 4V 60 μs | rigidity = 0 tremor = 0 | rigidity = 0 tremor = 0 | rigidity = 1 tremor = 0 |
| PD10 | 57 | L | 10 | 21 | 1-2+ 168 Hz 4V 60 μs | rigidity = 0 tremor = 1 | rigidity = 0 tremor = 0 | rigidity = 0 tremor = 2 |
| PD12 | 64 | L | 38 | 65 | 1-0+ 146 Hz 4V 60 μs | rigidity = 2 tremor = 1 | rigidity = 1 tremor = 0 | rigidity = 1 tremor = 0 |
| PD17 | 63 | R | 32 | 48 | 1-3+ 155 Hz 4V 60 μs | rigidity = 2 tremor = 0 | rigidity = 1 tremor = 0 | rigidity = NA tremor = NA |
| PD21 | 53 | R | 11 | 30 | 1-2+ 143 Hz 4V 60 μs | rigidity = 1 tremor = 0 | rigidity = 0 tremor = 0 | rigidity = 1 tremor = 0 |
| PD23 | 64 | R | 20 | 33 | 0-3+ 145 Hz 5V 60 μs | rigidity = 3 tremor = 1 | rigidity = 2 tremor = 1 | rigidity = 2 tremor = 2 |
| PD25 | 67 | L | 9 | 16 | 1-2+ 153 Hz 4V 60 μs | rigidity = 1 tremor = 1 | rigidity = 1 tremor = 1 | rigidity = 1 tremor = 1 |
| PD27 | 64 | L | 4 | 11 | 1-2+ 144 Hz 4V 90 μs | rigidity = 0 tremor = 0 | rigidity = 0 tremor = 0 | rigidity = NA tremor = NA |
| PD28 | 68 | L | 35 | 49 | 1-2+ 174 Hz 4V 60 μs | rigidity = NA tremor = NA | rigidity = NA tremor = NA | rigidity = NA tremor = NA |
| PD29 | 65 | L | 17 | 30 | 0-3+ 140 Hz 4V 60 μs | rigidity = 3 tremor = 0 | rigidity = 2 tremor = 0 | rigidity = 3 tremor = 0 |
| PD32 | 56 | R | 24 | 37 | 1-2+ 147 Hz 4V 60 μs | rigidity = 1 tremor = 2 | rigidity = 0 tremor = 0 | rigidity = 1 tremor = 0 |
| PD33 | 79 | R | 15 | 30 | 1-2+ 141 Hz 4V 60 μs | Rigidity = NA tremor = NA | rigidity = NA tremor = NA | rigidity = NA tremor = NA |
| PD34 | 59 | R | 16 | 47 | 1-2+ 155 Hz 4V 60 μs | rigidity = 0 tremor = 0 | rigidity = 0 tremor = 0 | rigidity = 0 tremor = 1 |
| PD35 | 74 | R | 27 | 48 | 1-2+ 195 Hz 4V 60 μs | rigidity = 0 tremor = 0 | rigidity = 0 tremor = 0 | rigidity = 0 tremor = 0 |
| PD37 | 73 | R | 18 | 39 | 1-2+ 213 Hz 4V 60 μs | rigidity = 2 tremor = 0 | rigidity = 1 tremor = 0 | rigidity = NA tremor = NA |
| Mean ± std | 63.1 ±7.0 | 9L/11R | 19.6 ±9.9 | 37.1 ±13.6 | c- = 0.8±0.4 c+ = 2±0.5 Hz = 163.8±23 V = 4 μs = 61.5±6.7 | rigidity = 1.2±1.0 tremor = 0.5±0.6 | rigidity = 0.5±0.7 tremor = 0.1±0.4 | rigidity = 1.1±0.8 tremor = 0.5±0.7 |

FIG. 24

| variables | Before DBS | During DBS | After DBS | P value Before vs during DBS | P value during vs after DBS |
|---|---|---|---|---|---|
| PAC β | 0.0015 | 0.0009 | 0.0013 | 0.0017 * | 0.07 |
| PAC phase | 0.74 | 0.63 | 1.00 | 0.94 | 0.87 |
| PAC max freq | 17.20 | 16.80 | 16.80 | 0.85 | 0.98 |
| Mean psd β | 1.54 | 1.48 | 1.49 | 0.13 | 0.65 |
| Max psd amp | 0.96 | 0.98 | 0.91 | 0.37 | 0.17 |
| Max psd freq | 19.04 | 20.21 | 18.75 | 0.16 | 0.10 |
| Mean psd γ | -0.61 | -0.62 | -0.64 | 0.50 | 0.97 |

FIG. 25

| Variables | Before DBS | During DBS | after DBS | P value before vs during DBS | P value during vs after DBS |
|---|---|---|---|---|---|
| PAC β hold | 0.0039 | 0.0033 | 0.0038 | 0.042* | 0.064 |
| PAC β prep | 0.0026 | 0.002 | 0.0027 | 0.007* | 0.003* |
| PAC β mvt | 0.0017 | 0.0014 | 0.0017 | 0.02* | 0.002* |
| P value hold vs prep | 0.007 | 0.012 | 0.009 | | |
| P value prep vs mvt | 0.042 | 0.003 | 0.005 | | |

FIG. 26

| Variables | Before DBS | During DBS | after DBS | P value before vs during DBS | P value during vs after DBS |
|---|---|---|---|---|---|
| mean β hold | 0.79 | 1.26 | 0.61 | 0.27 | 0.30 |
| β changes prep | -4.67 | -7.70 | -5.21 | 0.06 | 0.08 |
| β changes mvt | -14.02 | -13.97 | -13.19 | 0.97 | 0.42 |
| P value hold vs prep | 0.00049* | 0.00049* | 0.00049* | | |
| P value prep vs mvt | 0.00049* | 0.00098* | 0.00049* | | |
| P value hold vs mvt | 0.00049* | 0.00049* | 0.00049* | | |

FIG. 27

| Variables | Before DBS | During DBS | after DBS | P value before vs during DBS | P value during vs after DBS |
|---|---|---|---|---|---|
| mean γ hold | -0.20 | -0.58 | -0.76 | 0.34 | 0.73 |
| γ changes mvt | -0.42 | -1.41 | -0.63 | 0.38 | 0.27 |
| γ changes mvt | 4.29 | 2.35 | 2.97 | 0.11 | 0.42 |
| P value hold vs prep | 0.7910 | 0.1763 | 0.9697 | | |
| P value prep vs mvt | 0.0005* | 0.0010* | 0.0024* | | |
| P value hold vs mvt | 0.0024* | 0.0342 | 0.0049* | | |

METHODS AND SYSTEMS FOR TREATING NEUROLOGICAL MOVEMENT DISORDERS

CROSS-REFERENCE TO RELATED APPLICATIONS

Pursuant to 35 U.S.C. §119(e), this application claims priority to the filing date of U.S. Provisional Application Ser. No. 61/720,876 filed Oct. 31, 2012, the disclosure of which is herein incorporated by reference.

STATEMENT REGARDING FEDERALLY SPONSORED RESEARCH

This invention was made with government support under Grant No. R01 NS069779 awarded by the National Institutes of Health. The government has certain rights in the invention.

INTRODUCTION

Movement disorders arising from chronic brain diseases afflict millions of individuals. For example, Parkinson's disease (PD), the second most common such movement disorder, affects approximately 0.5% of the population. For many subjects suffering from the clinical presentations of such a movement disorder, including those with mid-stage PD that is no longer optimally improved by medication, the treatment of choice is chronic deep brain stimulation (DBS) of structures located in the basal ganglia.

Currently, deep brain stimulation in patients with PD and other movement disorders is often accomplished by surgical placement of a permanent electrode array within the thalamus or the basal ganglia (e.g., the subthalamic nucleus (STN) or globus pallidus internus (GPi)). The device is activated in the outpatient clinic by a neurologist or programming nurse. Many stimulation parameters can be varied noninvasively by programming the implanted pulse generator of the device. These parameters include stimulation amplitude (current or voltage), pulse width, frequency of stimulation, and which contact(s) of the multicontact array are activated. DBS devices have been implanted into >30,000 PD patients worldwide since 1993.

SUMMARY

The present disclosure provides methods for reducing the clinical presentations of a movement disorder in a subject. Aspects of the methods include measuring cortical local field potentials (LFPs) from the subject's brain, calculating a modulation index related to brain synchronization from the LFPs, and administering deep brain stimulation to the subject if the calculated modulation index is outside of a threshold range. Also provided are devices, systems, and kits for practicing the subject methods.

In certain embodiments, methods of the present disclosure include administering a first deep brain stimulus train to the subject; measuring cortical local field potentials (LFPs) from a surface of the subject's primary motor cortex using at least one electrode (e.g., by electrocorticography (ECoG) using at least one ECoG electrode, or by electroencephalography (EEG) using at least one EEG electrode); calculating, with a processor, a modulation index for synchronization of brain rhythms in the LFPs; administering a second deep brain stimulus train to the subject if the calculated modulation index is outside of a predefined threshold range; and continuing such steps in a manner effective to reduce the clinical presentations of the movement disorder. The LFPs may be measured using one or more electrodes, such as non-brain-penetrating electrodes. In certain aspects, at least one electrode for measuring LFPs is located at a position corresponding to the arm area of primary motor cortex M1 in the subject's brain, such as the posterior rim of motor cortex.

In other embodiments, methods of the present disclosure include measuring cortical local field potentials (LFPs) using at least one non-brain-penetrating electrode located at a position corresponding to an arm area of primary motor cortex M1 of the subject's brain (e.g., by electrocorticography (ECoG) using at least one ECoG electrode, or by electroencephalography (EEG) using at least one EEG electrode); calculating, with a processor, a modulation index for synchronization of brain rhythms in the LFPs; and administering a deep brain stimulus train to the subject if the calculated modulation index is outside of a predefined threshold range, wherein said administering is in a manner effective to reduce the clinical presentations of the neurological movement disorder. Such methods may further include calculating, with the processor, at least one parameter of the deep brain stimulation to change if the modulation index is outside of the predefined threshold range; receiving, via the processor, a user confirmation in response to a prompt to change said at least one parameter of the deep brain stimulation; and changing, with the processor, said at least one parameter of the deep brain stimulation; with such steps performed prior to administering the subsequent stimulus train to the subject.

The calculated modulation index may itself vary in practicing the subject methods, but is related to brain synchronization as manifested by an interaction of brain rhythms. In certain aspects, the modulation index is calculated by calculating a Kullback-Liebler-based modulation index, a mean vector length modulation index, applying a phase-amplitude coupling palette method, and/or calculating a phase-locking value. Where two or more modulation indices are calculated (e.g., two or more indices selected from a Kullback-Liebler-based modulation index, a mean vector length modulation index, applying a phase-amplitude coupling palette method, and calculating a phase-locking value), such indices may be combined—such as by using linear regression, nonlinear regression, weighted combination, and the like—to produce the calculated modulation index.

Moreover, the LFPs used to calculate a modulation index may vary greatly. In certain aspects, the LFPs may be filtered in one or more ways prior to calculation of the modulation index, such as to remove one or more frequencies, amplitudes, and the like prior to calculating the modulation index. For instance, in certain aspects the modulation index is calculated using LFPs filtered so as to include only frequencies from a certain range (e.g., about 15 Hz to about 30 Hz, about 25 Hz to about 100 Hz, etc.), and/or only amplitudes from a certain range (e.g., about 50 Hz to about 200 Hz). In certain aspects, the LFPs may be digitized to a certain sampling rate prior to calculating the modulation index, such as about 200 samples per second or more, including about 400 samples per second to about 2000 samples per second, or about 2000 samples per second or more.

The calculated modulation index may be used (e.g., by a processor) to cause one or more changes in the subject methods. For example, in certain embodiments the processor may change one or more parameters of the first deep brain stimulus train prior to administering the second deep brain stimulus train if the calculated modulation index is outside of the predefined threshold range. Thus, the first and second deep brain stimulus trains may be the same, or different. Where the first and second deep brain stimulus trains are different, one or more (e.g., 2 or more, including 3 to 5, 5 to 10, etc.) parameters may be changed from the first deep brain stimulus train to the second deep brain stimulus train. Such parameters may include, but are not limited to, the contact choice, amplitude, and/or frequency of such deep brain stimulation.

In certain embodiments, such changes may be made if the calculated modulation index is outside of a threshold range. The threshold range may be based on control values (e.g., reference standards, values obtained from a control population, and the like) and/or may be tailored for a particular subject. For a particular subject, threshold range may stay constant over time, or may vary over time.

In practicing the subject methods, the manner of administering deep brain stimulation may vary. For example, deep brain stimulation may include stimulating one or more portions of a subject's brain, such as the structures in the basal ganglia, including the subthalamic nucleus, the globus pallidus, and/or the like. Deep brain stimulation may be administered using one or more electrodes of an array. Stimulation electrodes may be arranged as a stimulation electrode array. Aspects of embodiments of the methods of the present disclosure include placing one or more electrodes, such as a stimulation electrode array, in the subject's brain so as to deliver deep brain stimulation.

In certain aspects, a pharmacological agent may also be administered to the subject, such as by infusion. Pharmacological agents of interest include, but are not limited to, levodopa, carbidopa, catechol O-methyltransferase inhibitors, monoamine oxidase inhibitors, dopamine agonists, anticholinergics, catecholamines, baclofen, benzodiazepines, tetrabenezine, diazepam, clonazepam, and lorazepam. Administration of a pharmacological agent to a subject may be achieved in various ways, including, but not limited to, oral, parenteral (e.g., subcutaneous, intramuscular, intradermal, intravenous and intrathecal), intraperitoneal, intravesicular, etc., administration. In certain aspects, administration is controlled by a processor configured to administer the pharmacological agent (e.g., using a drug delivery device). The processor may change one or more parameters of such administration if the calculated modulation index is outside of the threshold range.

A wide variety of subjects and conditions may be treated using methods of the present disclosure. In certain aspects, the subject exhibits clinical presentations of a neurological movement disorder, such as Parkinson's disease and/or dystonia. Suitable subjects include those that have been diagnosed with a neurological movement disorder. Subjects suitable for the methods of the present disclosure include mammals (e.g., humans).

Also provided by the present disclosure are devices that may be used in practicing the subject methods. In certain embodiments, devices of the present disclosure include an input configured to receive cortical local field potentials (LFPs) from at least one electrode; an output configured to be in electronic communication with a pulse generator for administering deep brain stimulation; a processor in electronic communication with the input and the output, the processor programmed to calculate a modulation index related to brain synchronization from the LFPs received from the input; and change at least one parameter of the pulse generator based at least in part on the value of the modulation index. A device may include a number of additional components, such as a display (e.g., a display including a user interface), drug delivery device, data logging element(s), and/or user input elements (e.g., buttons, dials, and the like).

The present disclosure also provides systems that may be used in practicing the subject methods. In certain embodiments, systems of the present disclosure include a pulse generator configured to administer deep brain stimulation to the subject; a subdural electrode adapted to record cortical local field potentials (LFPs) from the surface of the primary motor cortex of the subject; a processor in electronic communication with the pulse generator and the subdural electrode; and computer-readable medium with stored programming embodying an algorithm for treating a subject having clinical presentations of a neurological movement disorder in accordance with a method of the present disclosure, wherein the computer-readable medium is operably coupled to the processor.

In other aspects, systems of the present disclosure include a pulse generator configured to administer deep brain stimulation to the subject; a subdural electrode adapted to record cortical local field potentials (LFPs) from a surface of the primary motor cortex of the subject; and a data analyzer in electronic communication with the pulse generator and the subdural electrode, the data analyzer comprising: a processor programmed to: calculate a modulation index for synchronization of brain rhythms in the LFPs; and administer deep brain stimulation to the subject via the pulse generator if the calculated modulation index is outside of a predefined threshold range. Systems may include one or more additional devices (e.g., a drug delivery device), as shall be described more fully herein.

BRIEF DESCRIPTION OF THE DRAWINGS

The invention may be best understood from the following detailed description when read in conjunction with the accompanying drawings. Included in the drawings are the following figures:

FIG. 3, Panel B, FIG. 3, Panel D, and FIG.

4, Panel D). Panel B: Boxplots showing the stronger phase-amplitude coupling observed in PD compared to cranio-cervical dystonia and to the interictal recordings in epilepsy patients. The horizontal lines represent the medians of the individual subjects' mean MIs (computed over the range shown in FIG. 2, Panel B), the boxes represent the 25-75% and the vertical dashed lines indicate the minimum and maximum coupling observed in each disease state (*p<0.01; Kruskal-Wallis). Panel C: Phase-amplitude coupling in the three different disease states during a movement task. Modulation indices were averaged for all individual subjects within each disease group as in Panel A. Panel D: Boxplots showing stronger phase-amplitude coupling observed in PD compared to dystonia and epilepsy (*p<0.01; Kruskal-Wallis). Medians and ranges calculated as described for Panel B.

Figure 4:
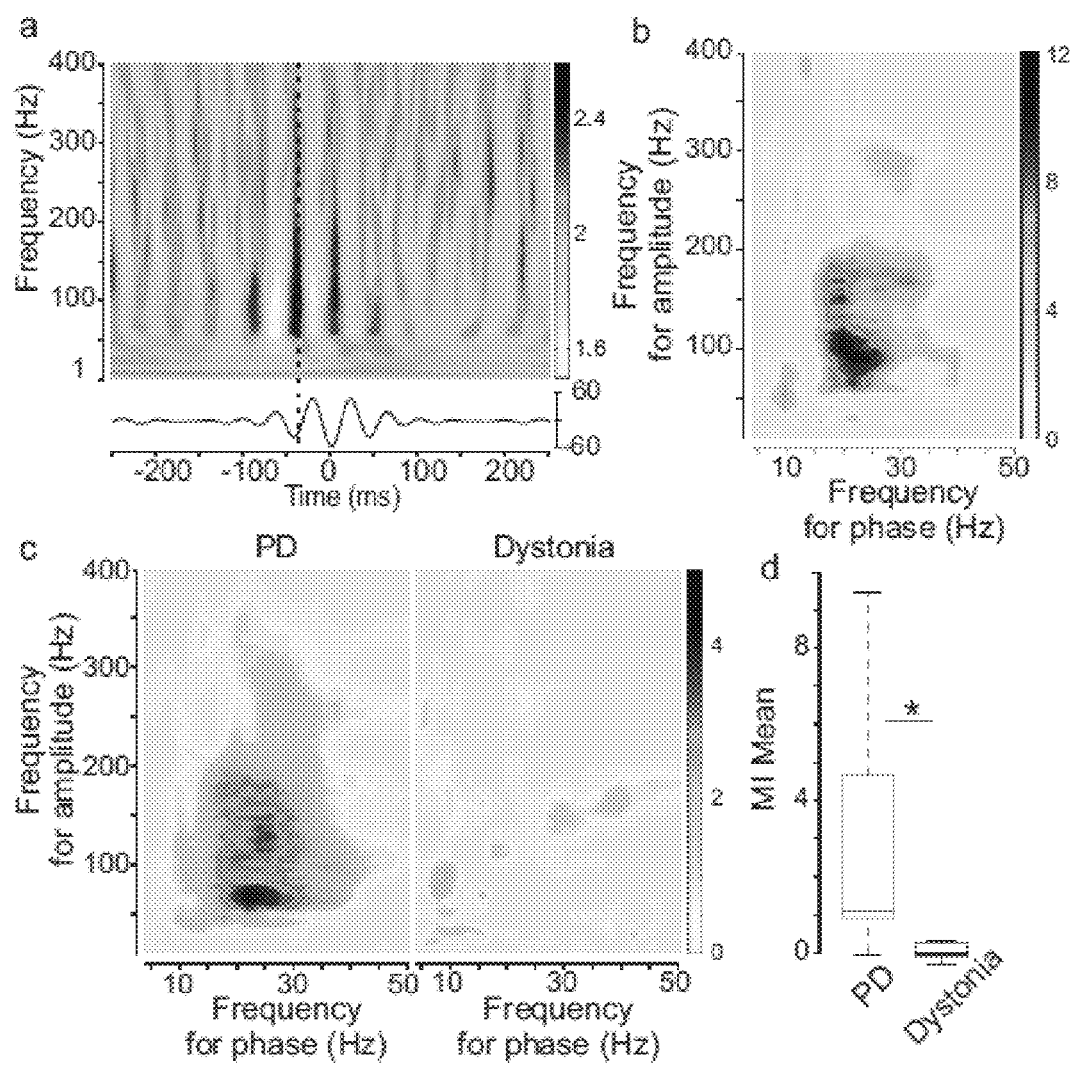

FIG. 4, Panels A-D show cross-structure (STN-M1) phase-amplitude coupling. Panel A: M1 scalogram aligned on the beta troughs of the STN LFP. M1 LFP signals were filtered at different frequencies and aligned on the trough of the beta STN rhythm (13-30 Hz, lower part of the panel). The black dotted vertical line shows the strongest cortical modulation, which precedes the beta trough by 42 ms. Panel B: Example of STN-M1 phase-amplitude coupling plot observed in a PD patient (PD8). The phase and amplitude signals were extracted from STN LFPs and from the M1 LFPs, respectively. Panel C: STN-M1 Modulation indices were averaged across all PD patients (right) and all dystonia patients (left). Panel D: Boxplots showing a significant difference in the phase-amplitude coupling between PD and dystonia (*p<0.01; Kruskal-Wallis). Medians and ranges calculated as described in FIG. 2, Panel B.

Figure 5:
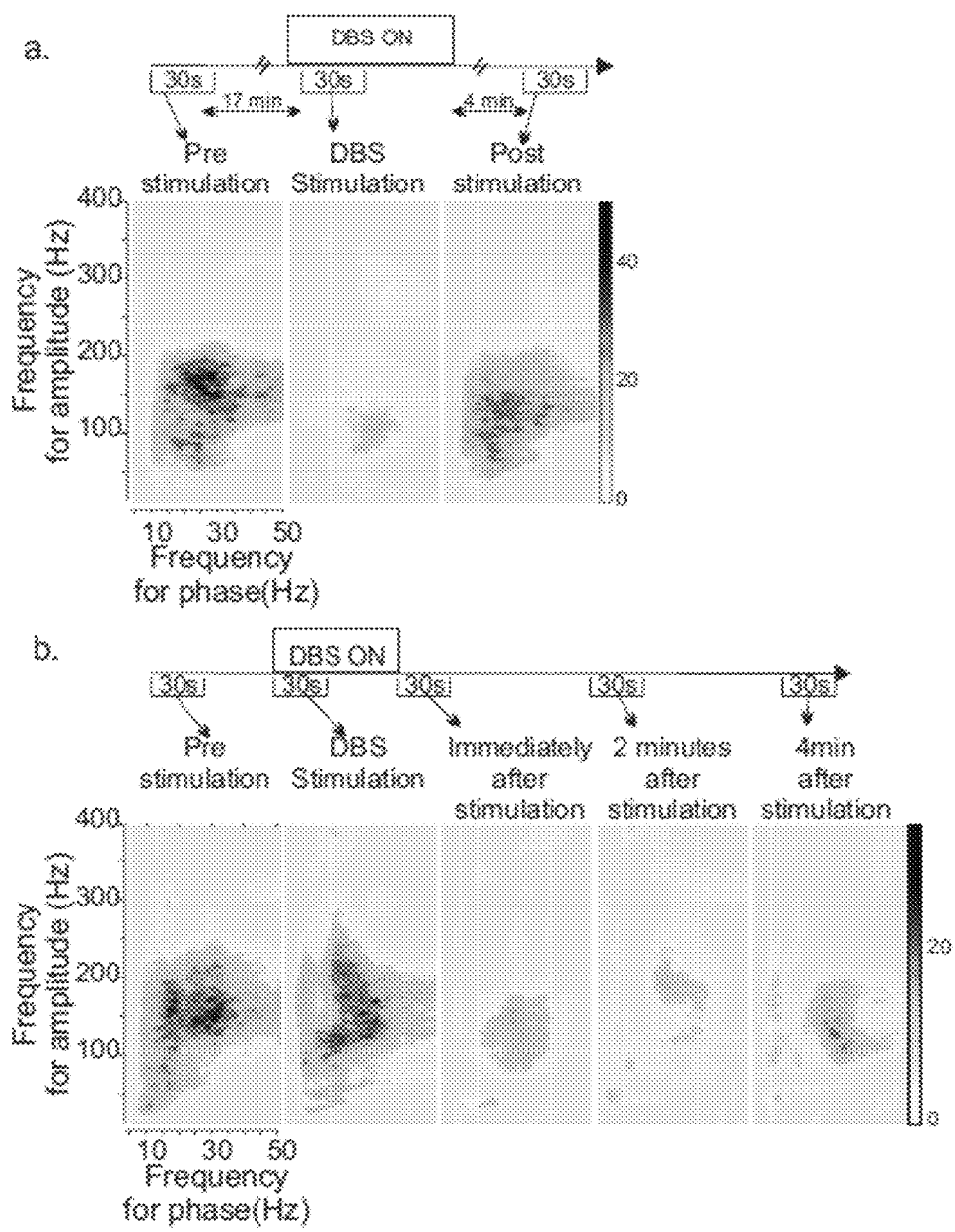

FIG. 5, Panels A-B are examples of the effect of acute therapeutic subthalamic stimulation on phase-amplitude coupling in the resting state. Panel A: Individual example showing a rapid reduction of phase-amplitude coupling due to acute stimulation (subject 10). This effect had partially washed out by 4 minutes after cessation of stimulation. The upper panel represents the time line of the different recordings and the time period selected to compute the phase-amplitude diagrams. Breaks in the time line indicate an interruption of the recordings. Panel B: Example of a more delayed effect of DBS on phase-amplitude coupling (subject 13). From this continuous recording, 5 periods have been selected to compute the phase-amplitude coupling as shown by the time line.

Figure 6:
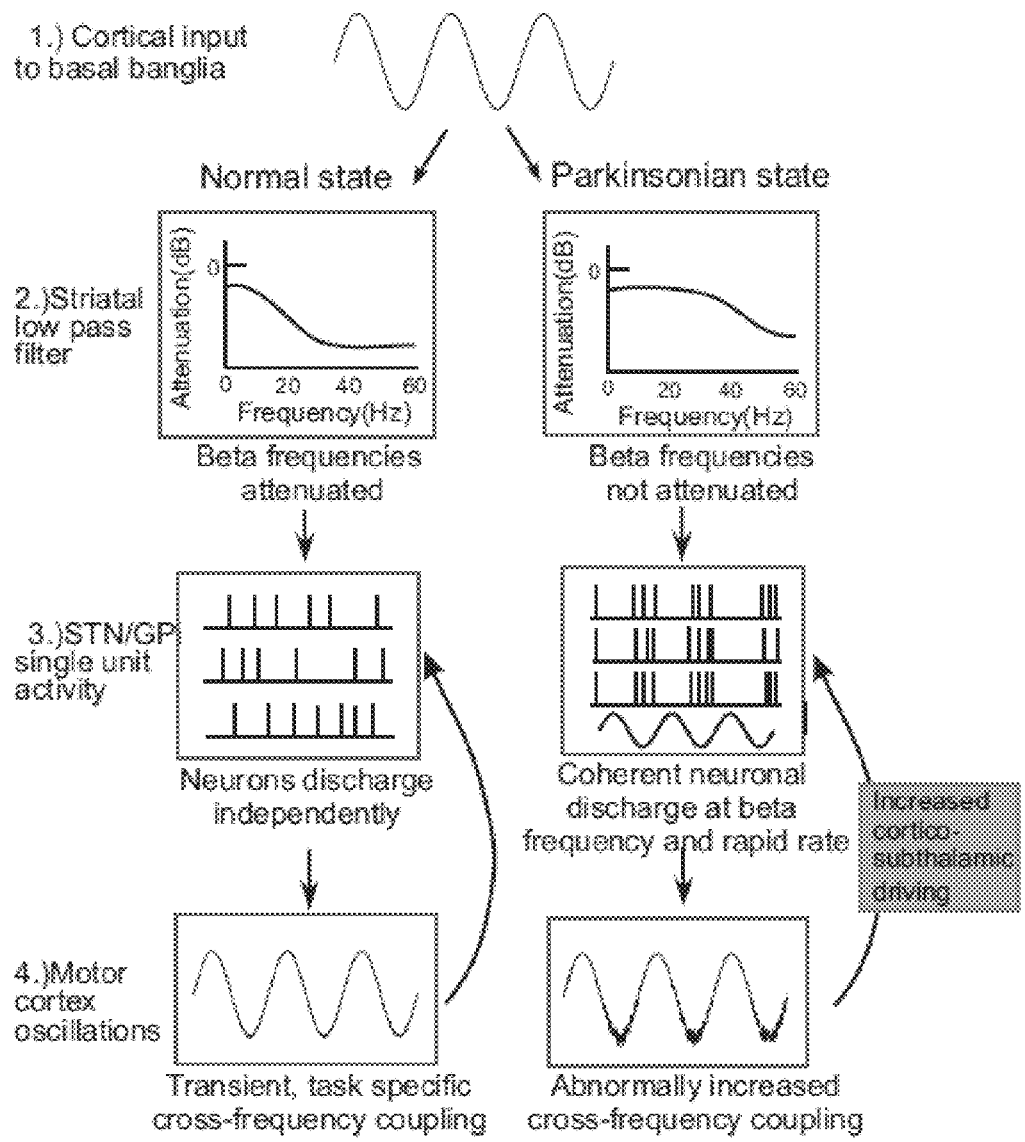

FIG. 6 is a model of cortex-basal-ganglia interactions in the normal (left) and Parkinsonian (right) states. Part 1: In general, cortical input to the striatum has a strong beta oscillatory component regardless of disease state. Part 2: The normal cortico-striatal circuitry acts as a low pass filter with significant beta band attenuation, but the dopamine-denervated striatum produces less beta attenuation. Part 3: In the Parkinsonian state, STN and GPi neurons have excessively synchronized activity in the beta band due to the change in the striatal filter. Part 4: In the Parkinsonian state, excessively coherent basal ganglia beta band neuronal discharge drives M1 to have abnormally increased coupling between beta phase and broadband gamma amplitude. This in turn reinforces increased STN beta synchrony and excessive STN firing rate via the "hyperdirect" cortico-subthalamic pathway (curved arrow).

Figure 7:
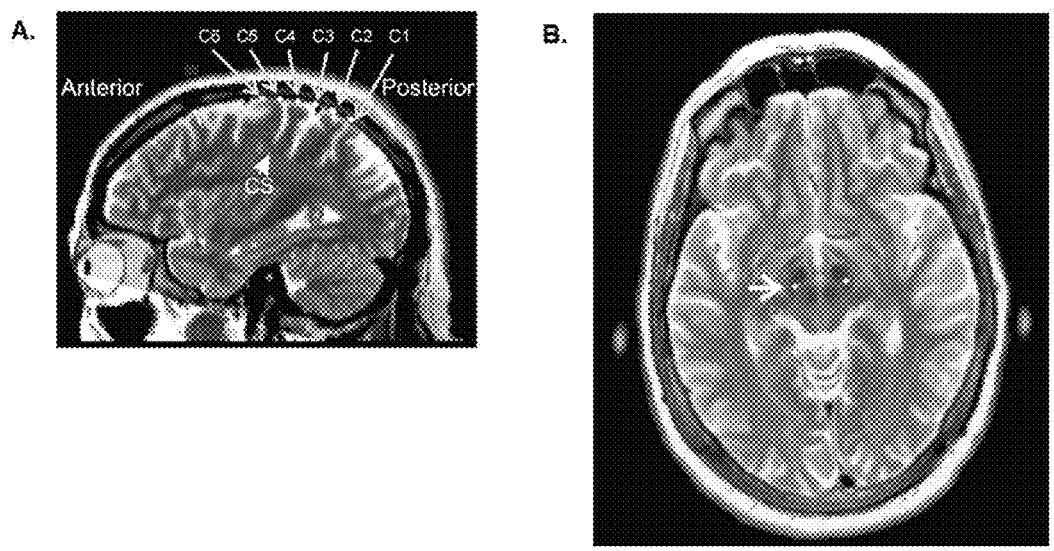

FIG. 7, Panels A-B depict localizing recording electrodes. Panel A: Localization of subdural ECoG recording strip used to record cortical activity in PD and dystonia. Parasagittal view of the intra-operative computed tomography (CT) merged to the preoperative MRI on which the 6 contacts of the ECoG strip and the central sulcus (white arrow CS) can be observed. ECoG contacts were labeled from the most posterior 'C1' to the most anterior 'C6'. The contact immediately anterior to central sulcus is considered as the best contact to record the activity in M1 (C5 in this example). Panel B: Localization of the tip of the DBS lead in the STN. The lead location as it passes through the dorsal STN, determined from postoperative MRI, is here superimposed on the preoperative targeting MRI. The lead artifact is visible as a white signal void, and indicated by white arrow.

Figure 8:
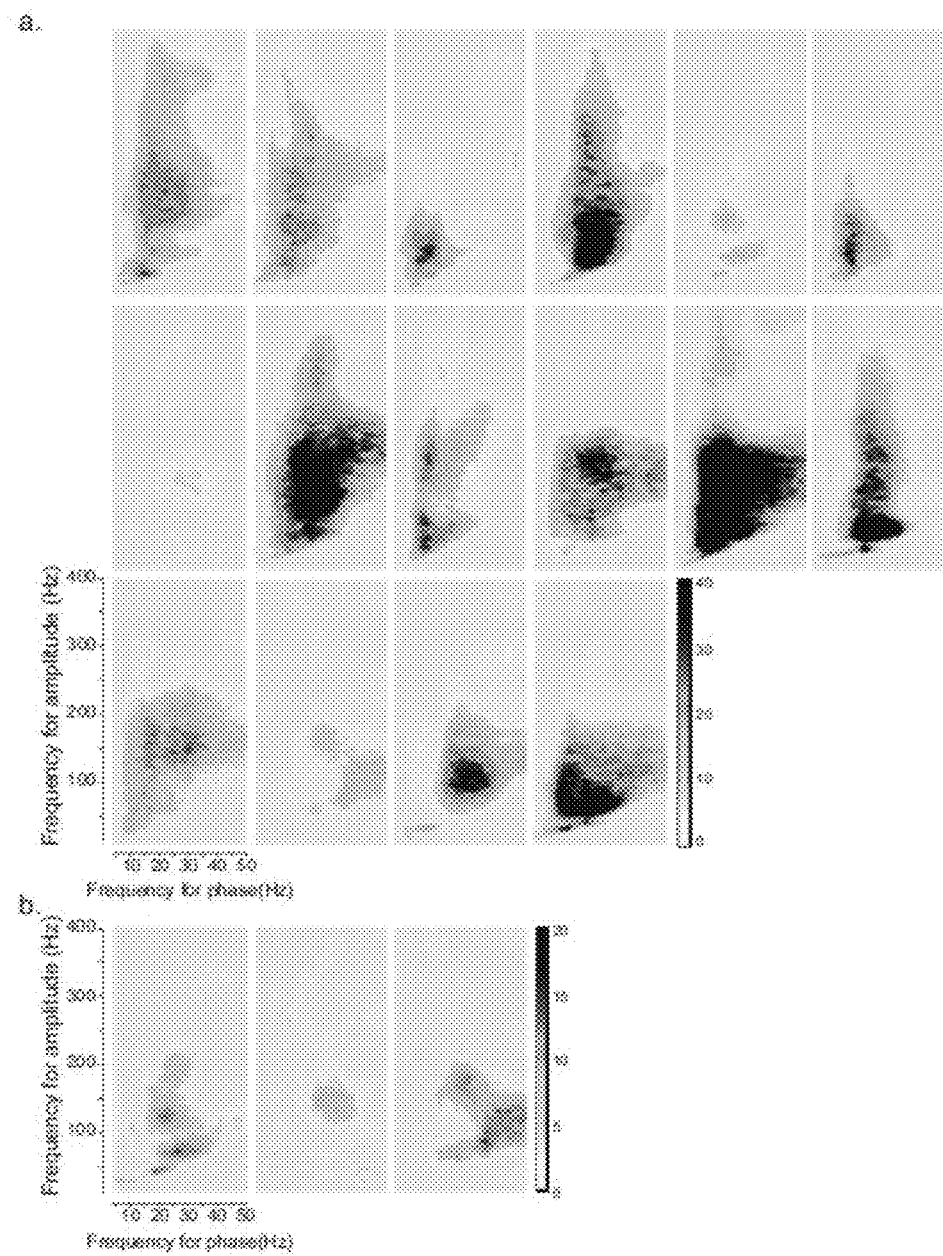

FIG. 8, Panels A-B depict M1 phase-amplitude coupling in PD. Panel A: Modulation index plots for each individual PD patient at rest. All patients had at least one point on the plot that crossed the threshold of statistical significance (for some combination of phase and amplitude frequency, Z>4.5). In PD, the maximal coupling was most often observed in the high beta band (20-30 Hz, 11 patients) although maximal coupling could also occur in the low beta band (13-20 Hz, 6 patients). Panel B: 3 PD patients (pt 5, 7, 14) showed relatively less phase-amplitude coupling; but nevertheless had significant coupling (>4.5) for several combinations of phase and amplitude frequencies as shown on a zoomed in color scale. This figure is related to FIG. 4, Panels A-D.

Figure 9:
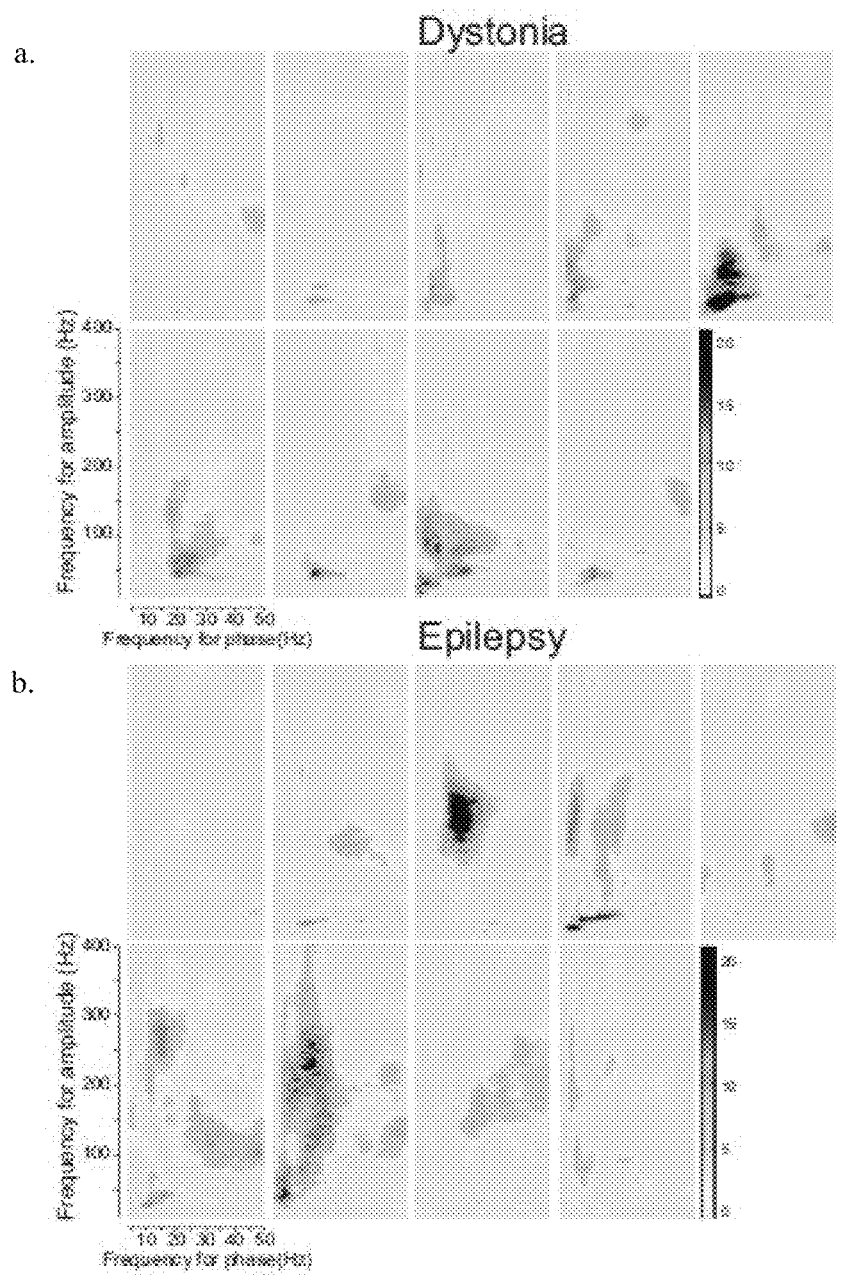

FIG. 9, Panels A-B are M1 phase-amplitude modulation index plots for each individual patient at rest in Panel A, cranio-cervical dystonia, and Panel B, epilepsy. All dystonia patients and 7 of 9 patients with epilepsy had at least one point on the plot that crossed the threshold of statistical significance (for some combination of phase and amplitude frequency, Z>4.5). Note the difference in scale between this figure and FIG. 8, Panel A, consistent with the generally greater magnitude of phase-amplitude coupling for PD patients. This figure is related to FIG. 4, Panels A-D.

Figure 10:
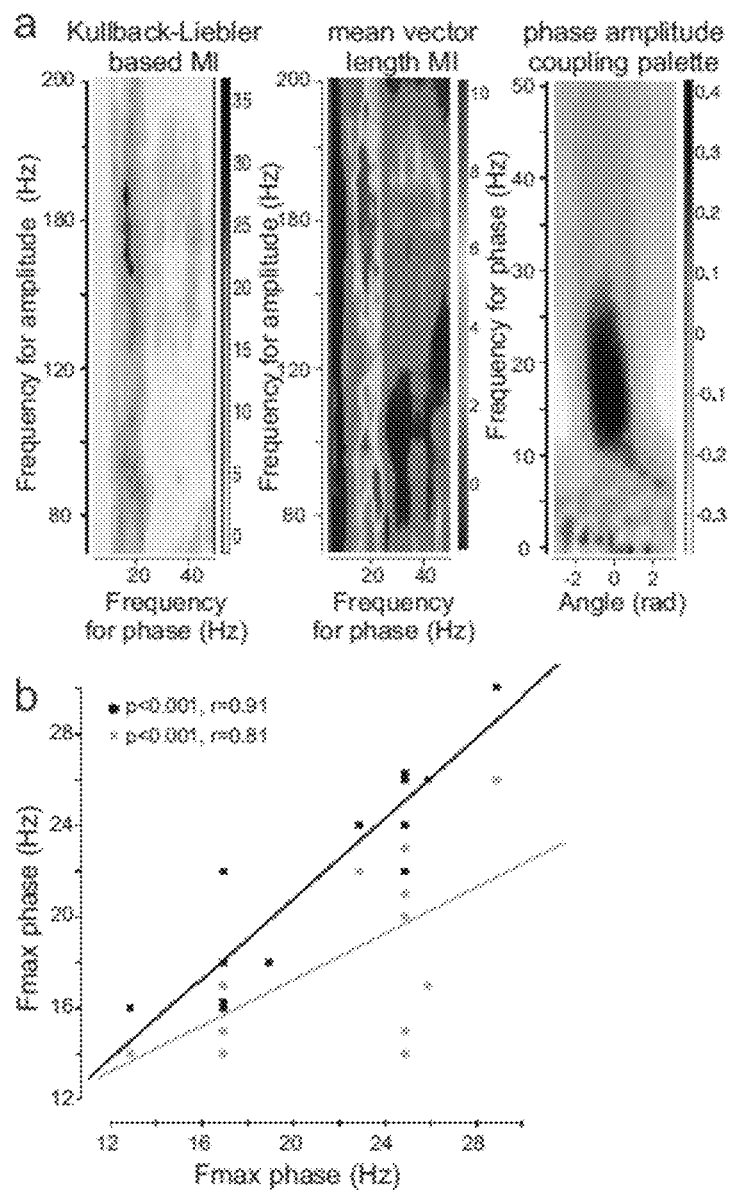

FIG. 10, Panels A-B show the similarity of M1 phase-amplitude coupling in PD using three different computational methods to quantify the magnitude of coupling across a range of phase frequencies and amplitude frequencies. Panel A: Example of phase-amplitude coupling plots computed using the "Kullback-Liebler (KL)-based modulation index," left. The "mean vector length modulation index," middle. The "phase-amplitude coupling palette" method, right, for an individual patient. On all three plots, the strongest coupling is observed between the amplitude of broadband gamma and the phase of beta rhythm (15-20 Hz). Panel B: Optimal phase frequencies for all PD subjects, showing similar results for the three computational methods. For each PD patient, the frequency for phase involved in the strongest coupling was determined using each method and linear regressions were performed. Comparison between KL-based modulation index and the mean vector length modulation index is represented by black circles (p<0.001, r=0.91). Comparison between the KL-based modulation index and the phase-amplitude coupling palette is represented by gray circles (p<0.001, r=0.81).

Figures 11, 12:
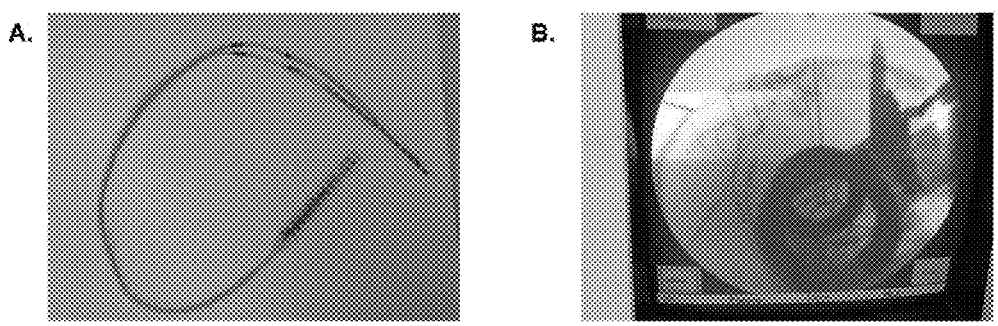

FIG. 11 is a table showing characteristics of M1-M1 and STN-M1 modulation indices observed in Parkinson's disease. Abbreviations: M1phase-M1 amp=modulation index computed using the phase of M1 and the amplitude of M1, STNphase-M1amp=modulation index computed using the phase of STN and the amplitude of M1, MI mean=average MI between 13-30 Hz, MI max=value of the maximal coupling, Fmax phase=Frequency for phase involved in the maximal coupling, Fmax amp=Frequency for amplitude involved in the maximal coupling, Pref phase=phase at which the maximal coupling occurred. All values were derived from the KL-based modulation index.

Figure 13:
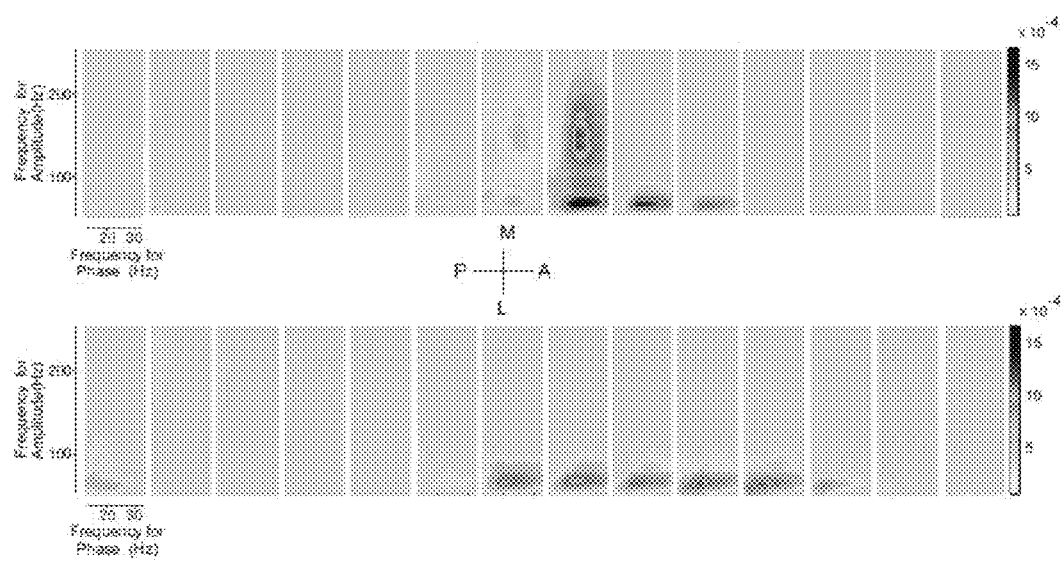

FIG. 12, Panels A-B show a 28-channel grid, and the placement thereof. Panel A: Picture of a 28 channel grid, composed of two rows of 14 contacts each. Panel B: Intra-op CT scan showing the 28 contacts of the grid of Panel A. Dark curve represents the motor cortex M1. The most posterior contact covering M1 is contact 8 on the first row and contact 21 on the second row. The circle shows those contacts relative to M1. This figures shows an example of a clinically practical high resolution strip electrode, implantable via a single 1.5 cm skull opening, that could be used for cortical recording FIG. 13 depicts resting state PAC calculated from each of the 28 electrodes from a grid as shown in FIG. 12, Panels A-B. Upper panel depicts PAC observed in contacts 1-14 from the 28-channel grid. Contact 8 (most posterior contact covering the motor cortex M1) shows the strongest PAC. Contacts 9 and 10 (still over M1) show low PAC. Lower panel shows is PAC observed in contacts 15-28 from the 28-channel grid. Contacts 21 to 25 (over M1) show low PAC. No contacts show a PAC as strong as the PAC observed in contact 8. The figure shows that the PAC signal is highly localized over the posterior primary motor cortex, and can be measured from an electrode of 1 mm diameter, as well as the larger 3 mm electrodes shown in FIG. 7, Panel A. (A, anterior; P, posterior; M, medial; L, lateral).

Figure 14:
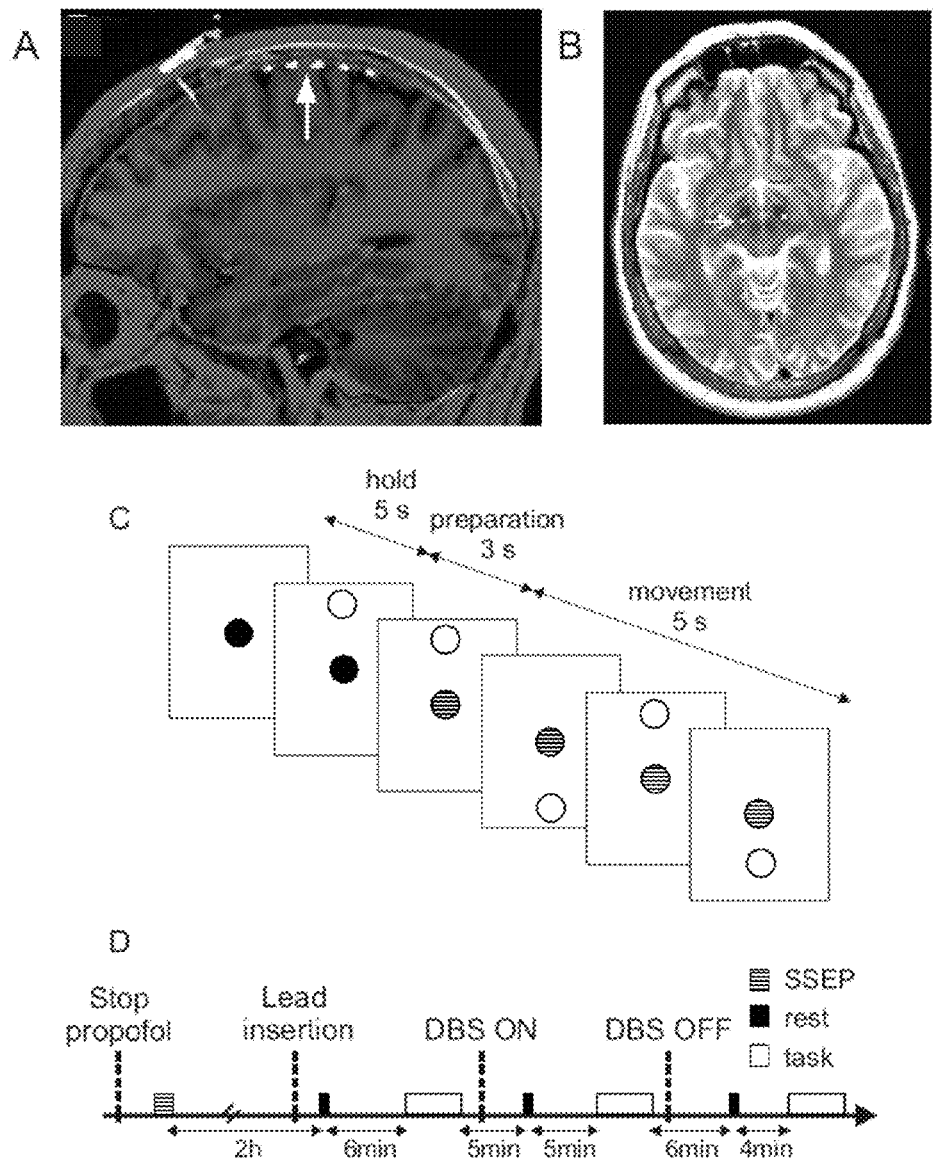

FIG. 14, Panels A-D depict device localization, task paradigm, and timeline of recordings. Panel A shows the localization of a subdural ECoG strip used to record cortical activity. The six contacts of the ECoG strip (white dots) relative to the central sulcus (white arrow) can be observed on this parasagital view of the intraoperative CT scan merged with the preoperative MRI scan. The most posterior contact is labelled C1 and the most anterior, used as the reference during recording, is C6. In this example, the contact defined as the closest to M1 is C5. Panel B shows the localization of the tip of the DBS electrode (arrow) at the base of STN, on an axial view of the intraoperative CT scan merged with the preoperative MRI. Panel C is a description of an arm movement task. A single trial is represented. Each trial starts with a rest period of 5 seconds during which the patient maintains gaze on a central red dot (here, depicted as a solid dot). Then, the 'target', a blue dot (here, depicted as a white dot), occurs at the upper or lower edge of the screen (the position was randomized). The patient was instructed to touch the target with the index finger after the central dot turns green (here, depicted as a dot with horizontal striping). This task permits the distinction of 3 phases: the "hold", the "preparation" and the "movement" phases. Panel D shows a typical timeline for lead insertion, recording, and stimulation. Rectangles represent the different data collection events as follows: Horizontal striping, SSEP; solid, rest; white; arm movement task. The time between recordings is indicated under the horizontal arrows in minutes.

Figure 15:
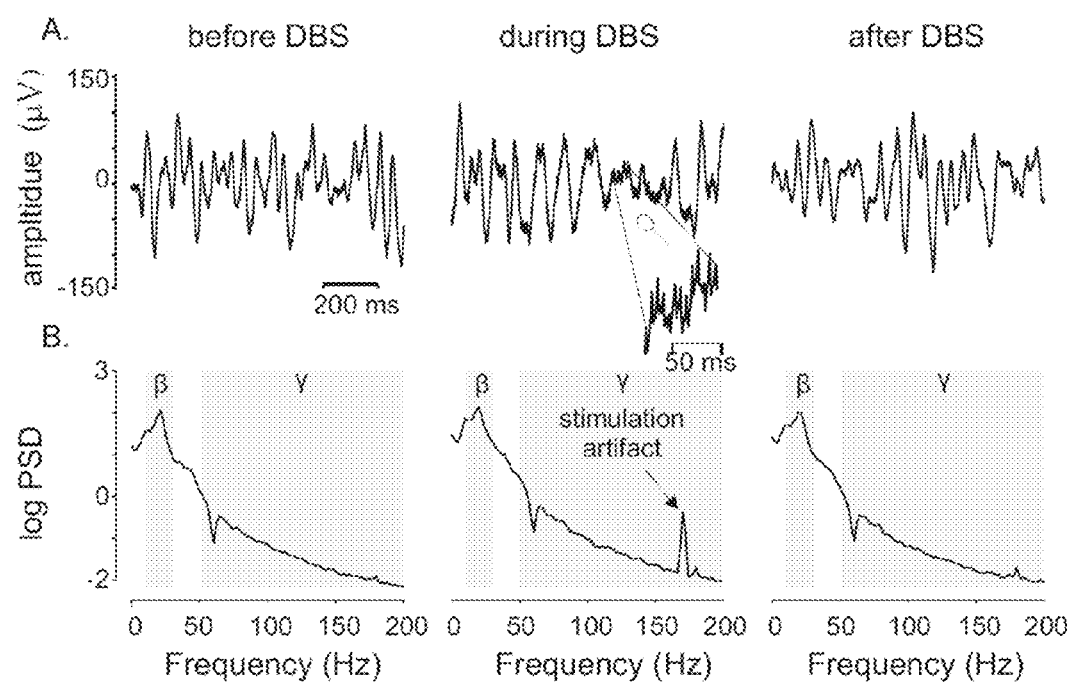

FIG. 15, Panels A-B depict example M1 recordings and their spectral characteristics, prior to filtering the stimulation artifact, in a single patient. Panel A shows M1 LFPs before (left panel), during (middle panel) and after STN stimulation (right panel). Panel B shows the log power spectral density for each recording in Panel A. A small artifact of stimulation can be observed on the zoomed LFP (Panel A, middle) and the corresponding log PSD (arrow, Panel B, middle). A peak in the beta band can be observed in each condition. Grey rectangles indicate beta band and broadband gamma.

Figure 16:
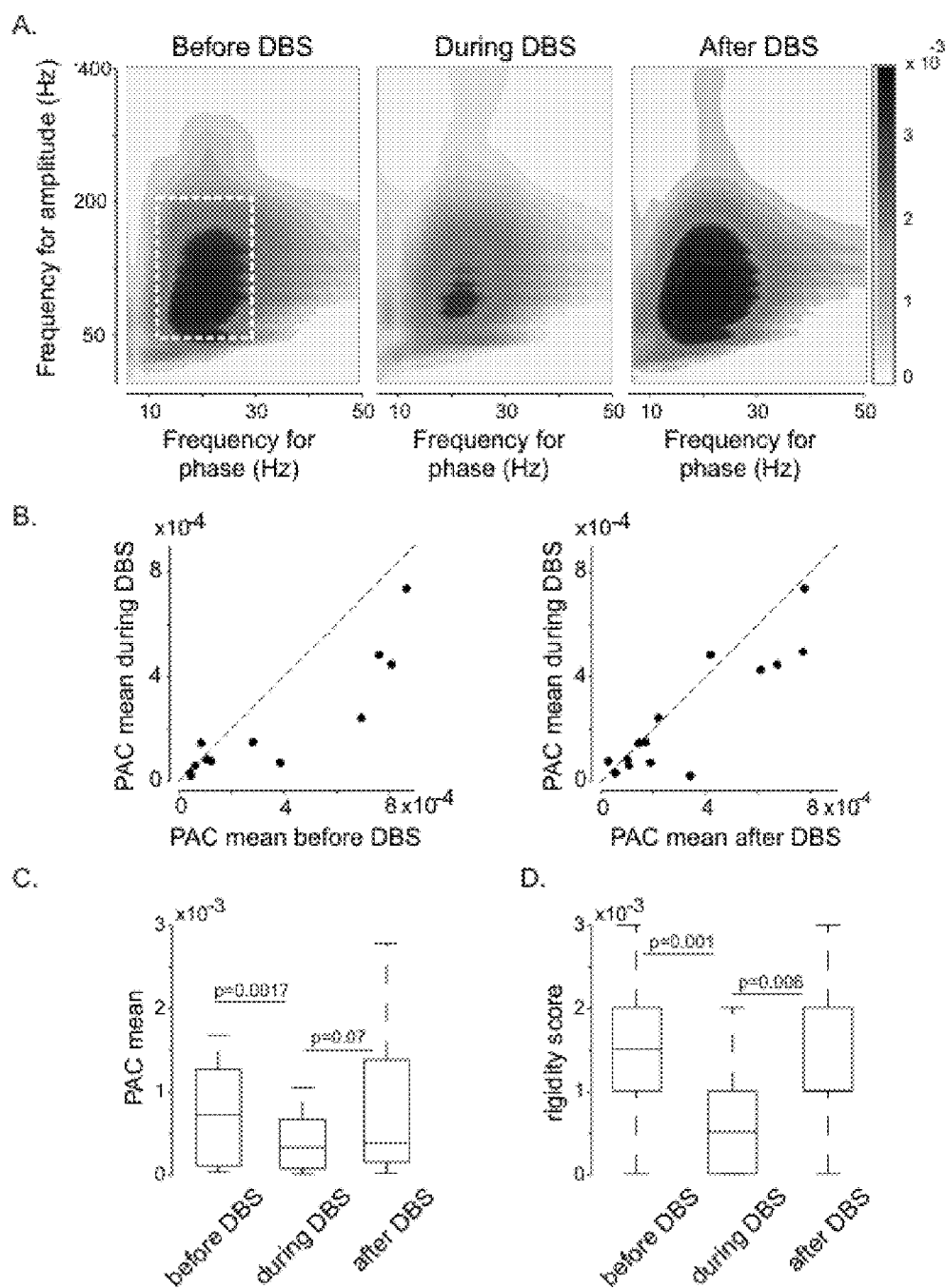

FIG. 16, Panels A-D depicts data demonstrating that acute therapeutic STN stimulation reduces PAC in the resting state. Panel A shows a representative example of phase-amplitude coupling observed in the M1 of a PD patient before (left panel), during (middle panel) and after STN stimulation (right panel). The warmest colors represent the strongest coupling. The white dotted box (left panel) shows the range of frequencies over which modulation indices were averaged to generate the statistical comparison between stimulation conditions. In Panel B, average phase-amplitude coupling observed during DBS is plotted versus that observed before DBS (left panel) and after DBS (right panel). Each dot represents one patient. In Panel C, a boxplot shows the significant and partly reversible reduction of PAC during STN DBS. In Panel D, a boxplot shows the therapeutic reversible effect of DBS on patient's rigidity.

Figure 17:
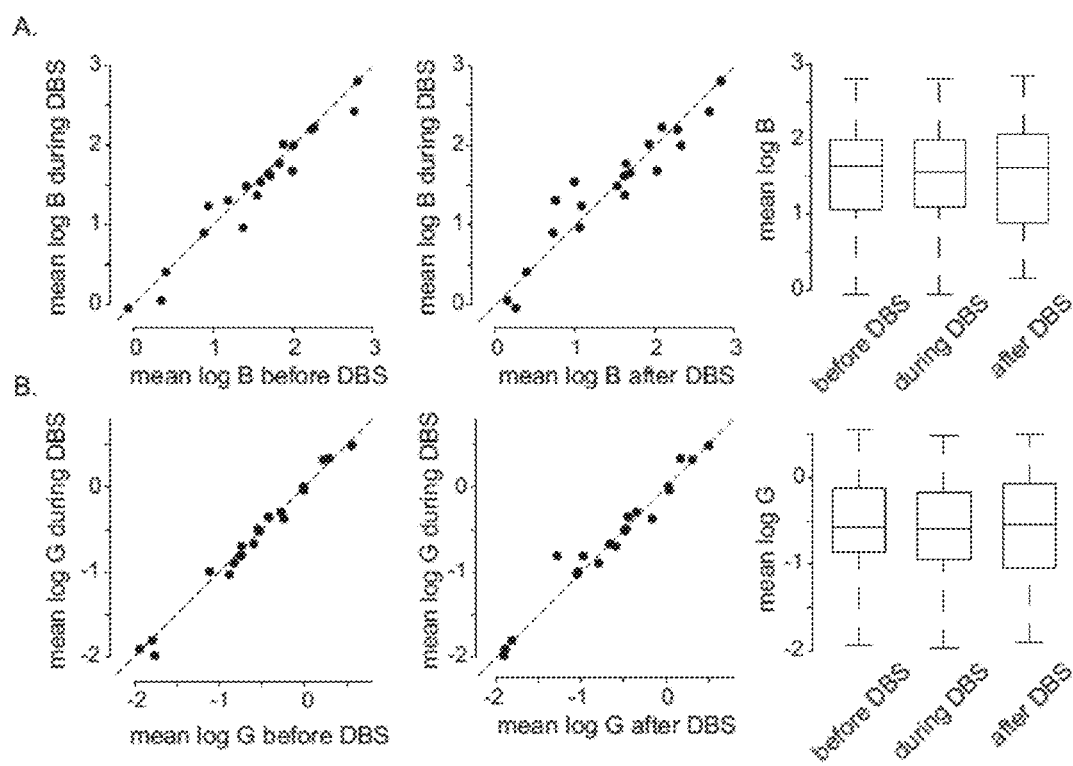

FIG. 17, Panels A-B depict data demonstrating that DBS does not affect resting state power spectral density. Panel A shows mean beta power for each subject before versus during DBS (left), for each subject after DBS versus during DBS (middle), and grouped data represented in boxplots (right). Panel B shows mean gamma power, represented in same manner as in Panel A.

Figure 18:
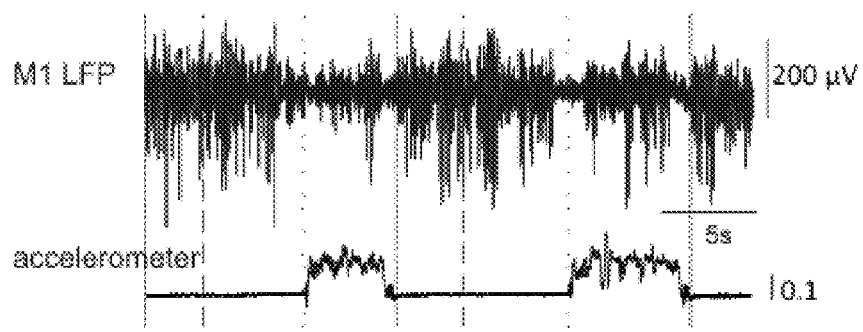
Figure 18:
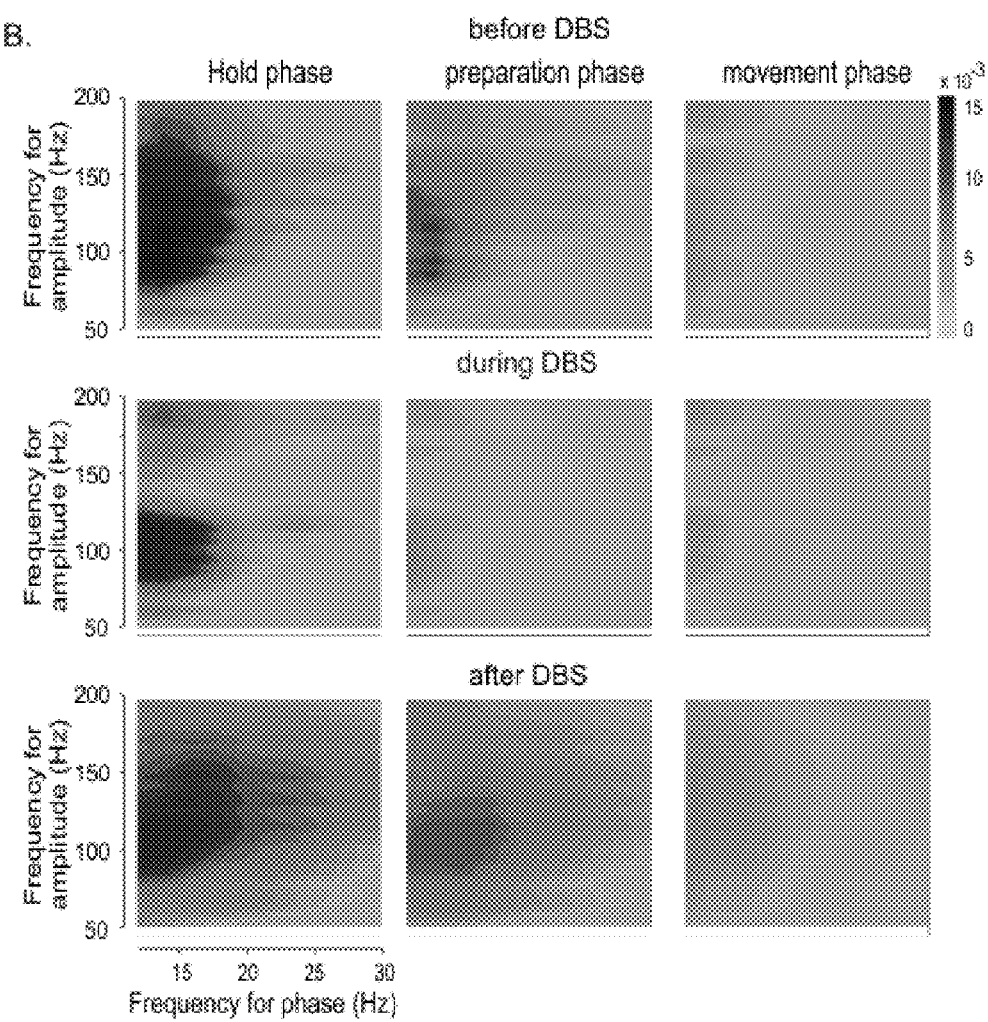

FIG. 18, Panels A-B depict examples of M1 LFP and phase-amplitude coupling during an arm movement task in one patient. Panel A shows M1 LFP (upper) and accelerometry (lower) during two trials of the task. Vertical dashed lines indicate the three phases of the task: from left to right, the first, fourth and seventh vertical dashed lines indicate the hold phase; the second and fifth vertical dashed lines indicate the preparation phase; and the third and sixth vertical dashed lines represent the movement phase. Panel B shows PAC in the three phases (left panels, hold; middle panels, preparation; right panels, movement) and in the three conditions of stimulation (top panels, before DBS; middle panels, during DBS; lower panels, after DBS. There is reduction of PAC from hold to movement preparation to movement execution, and DBS decreases PAC in all three phases of the task.

Figure 19:
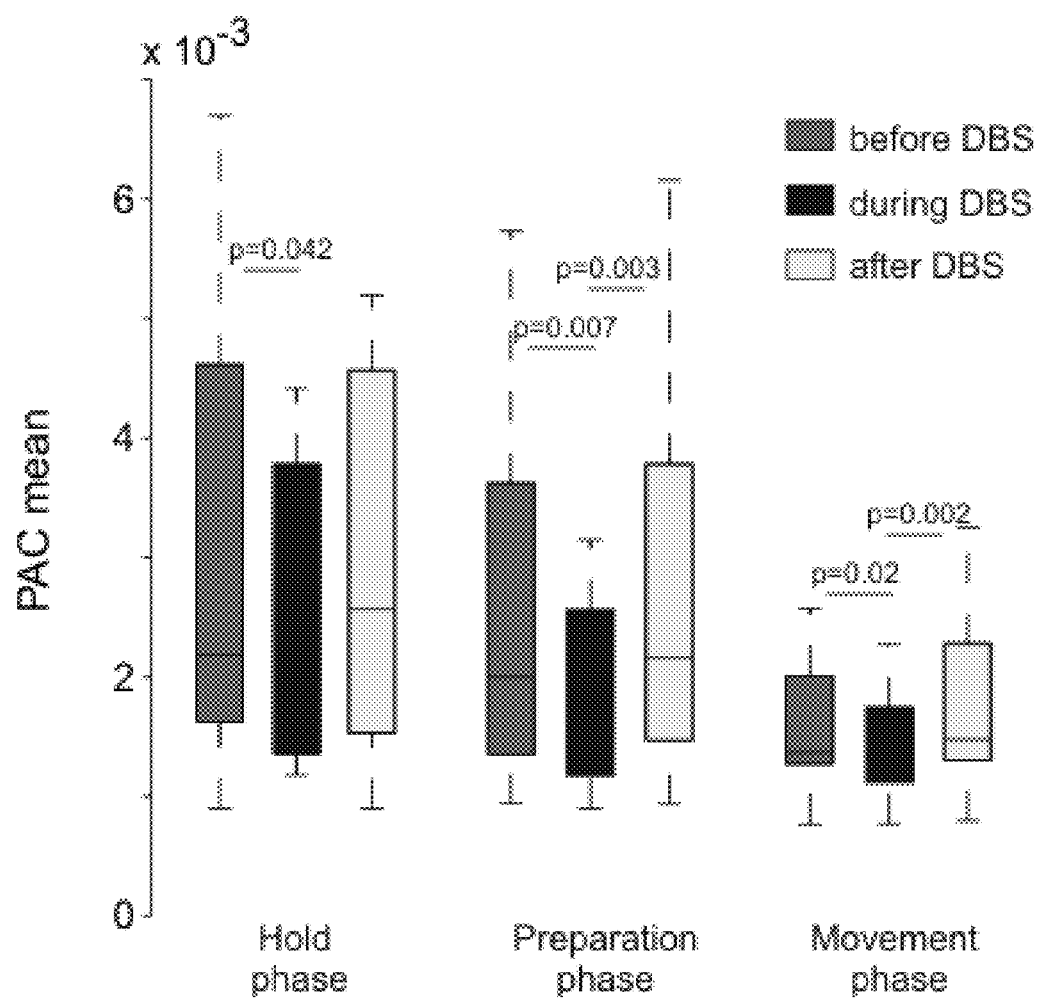

FIG. 19 depicts data demonstrating that both DBS and movement reduce PAC during an arm movement task. Medians and 25-75 percentiles are shown in the three phases of the task (hold, preparation and movement) before and during DBS stimulation. The three phases are represented in the x axis while the three conditions for each phase are, from left to right: before DBS; during DBS; and after DBS. A reduction of PAC is observed from hold phase to movement phase with an additional decrease of PAC during STN stimulation.

Figure 20:
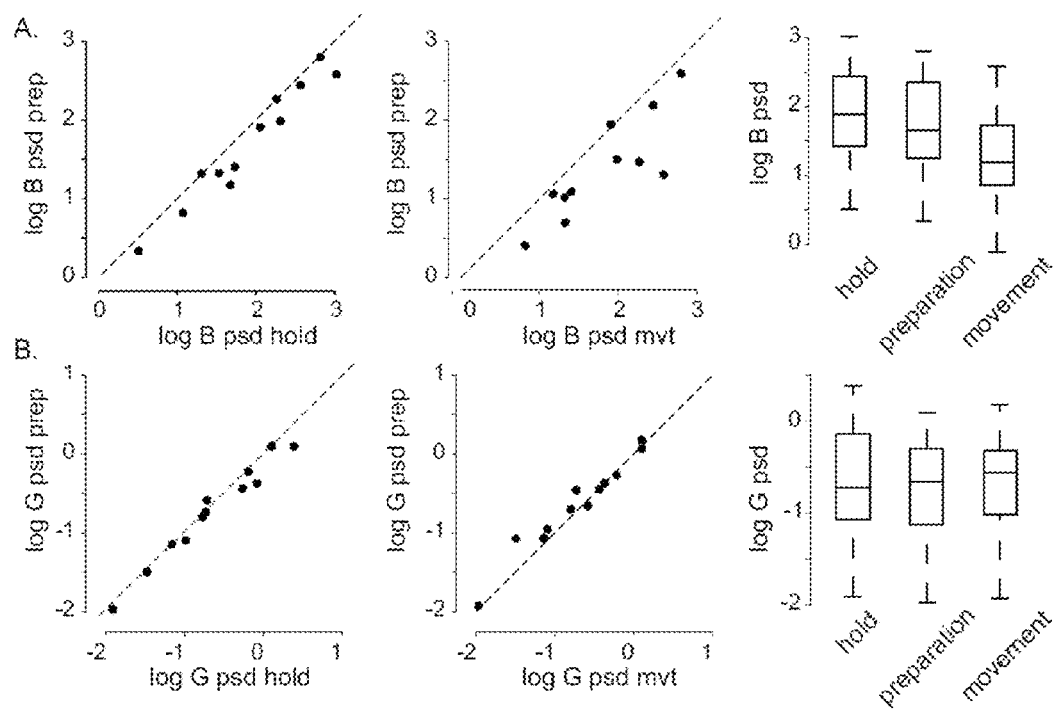

FIG. 20, Panels A-B depicts data demonstrating the effect of task phases on beta and gamma power, without DBS. Panel A shows mean log PSD in the beta band during movement preparation versus hold phase (left panel) and versus movement execution (middle panel). Each dot represents a patient. The boxplot shows the decrease of beta power from the hold to preparation phase and from preparation to execution. Panel B shows mean log PSD in the gamma band during movement preparation versus the hold phase (left panel) and versus movement execution (middle panel). M1 gamma power did not vary with the task.

Figure 21:
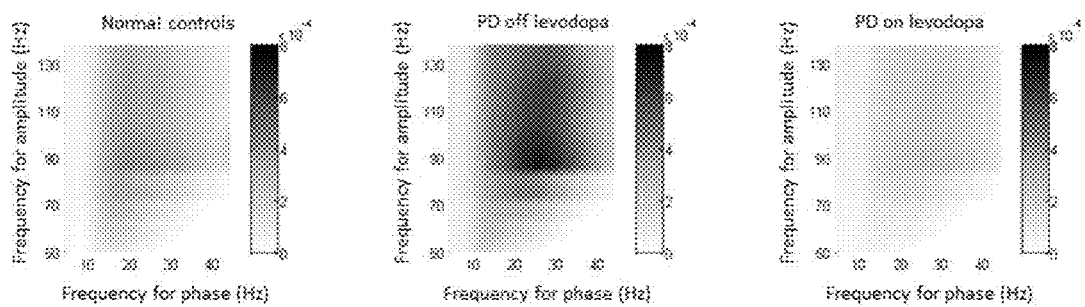

FIG. 21 depicts comodulogram data utilizing an existing archived data set on a cohort of PD patients who do not have DBS systems, and normal controls to validate the ability to detect PAC and reproduce earlier findings that PD patients have exaggerated PAC; and to show reduction in PAC in the levodopa-on state. Shown is average comodulogram across all subjects in each group from EEG contacts C3 and C4 (closest to M1 in each hemisphere), referenced to common average. Sixteen healthy age-matched controls (left) were compared with 15 PD patients off medication (middle) and on medication (right).

Figure 22:
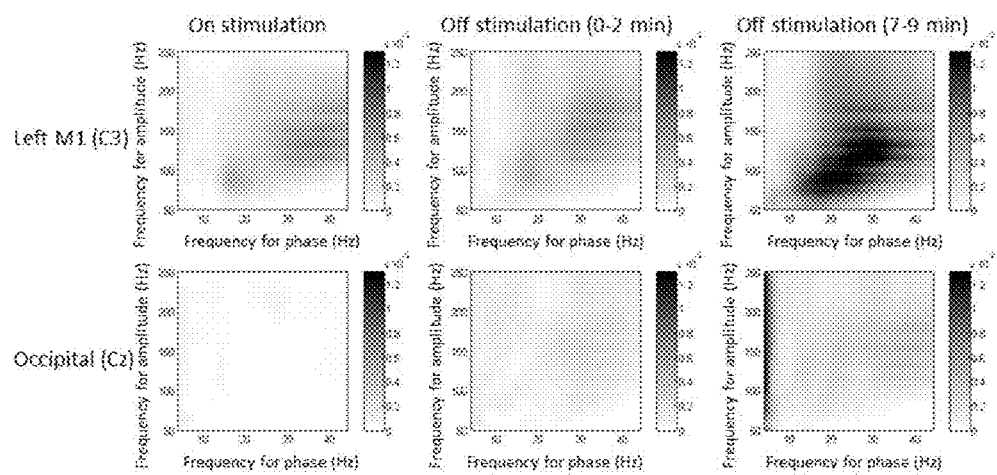

FIG. 22 depicts comodulogram data from a PD patient. The effect of chronic DBS on EEG was investigated. It was found that turning off therapeutic DBS (after 2 months of stimulation) resulted in a return of elevated PAC on a time-course of 2-5 minutes. Shown is a comodulogram derived from EEG contact C3 (the electrode closest to left M1), which corresponds to the more clinically effected side in this patient. Recordings were made during periods of alert rest during: chronic therapeutic DBS (2.2 V, monopolar STN stimulation, 180 Hz, 60 microseconds) (left); first two minutes after stopping DBS (middle); and 7-9 minutes after stopping DBS (right). Elevated PAC is more prominent over M1 (upper row) than in other areas (lower row).

FIG. 23 is a table showing individual subject parameters of a study conducted according to an embodiment of the present disclosure.

FIG. 24 is a table providing data that shows the effect of DBS at rest.

FIG. 25 is a table providing data that shows the effect of DBS on phase-amplitude coupling during a task.

FIG. 26 is a table providing data that shows the effect of DBS and behavioral state on log β.

FIG. 27 is a table providing data that shows the effect of DBS and behavioral state on log Y.

DETAILED DESCRIPTION

The present disclosure provides methods for reducing the clinical presentations of a neurological movement disorder in a subject. Aspects of the methods include measuring cortical local field potentials (LFPs) from the subject's brain, calculating a modulation index from the LFPs, and administering deep brain stimulation to the subject if the calculated modulation index is outside of a threshold range. Also provided are devices, systems, and kits for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the electrode" includes reference to one or more electrodes, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the present disclosure include methods for treating neurological movement disorders. Aspects of the methods include measuring cortical local field potentials (LFPs) from the subject's brain, calculating a modulation index from the LFPs, and administering deep brain stimulation to the subject if the calculated modulation index is outside of a threshold range.

The terms "movement disorder," "neurological movement disorder" or "neurological condition," as used herein, are used broadly and generically to refer to any brain disease, anomaly, or condition causing a subject to have abnormal voluntary and/or involuntary movements, or slow, reduced movements. Exemplary neurological movement disorders include, but are not limited to, Parkinson's disease, dystonia, Huntington's disease, essential tremor, anxiety, mood disorders, sleep disorders, obesity, anorexia, and chronic pain disorders.

A neurological movement disorder may be treated using embodiments of methods of the present disclosure. By "treatment," "treatment," or "treat" is meant that at least an amelioration of the symptoms associated with the condition afflicting the subject is achieved, where amelioration is used in a broad sense to refer to at least a reduction in the magnitude of a parameter, e.g., a symptom, associated with the condition being treated. As such, treatment includes a broad spectrum of situations ranging from slowing, delaying, or halting progression of a condition and/or a related symptom, up to and including completely eliminating the condition, along with any associated symptoms. Treatment therefore includes situations where the condition, or at least a symptom associated therewith, is completely inhibited, e.g., prevented from happening, or stopped, e.g., terminated, such that the subject no longer suffers from the condition, or at least the symptoms that characterize the condition. Treatment also includes situations where the progression of the condition, or at least the progression of a symptom associated therewith, is slowed, delayed, or halted. In such cases, a subject might still have residual symptoms associated the pathological condition, but any increase in the severity or magnitude of the symptoms is slowed, delayed, or prevented.

Figure 1:
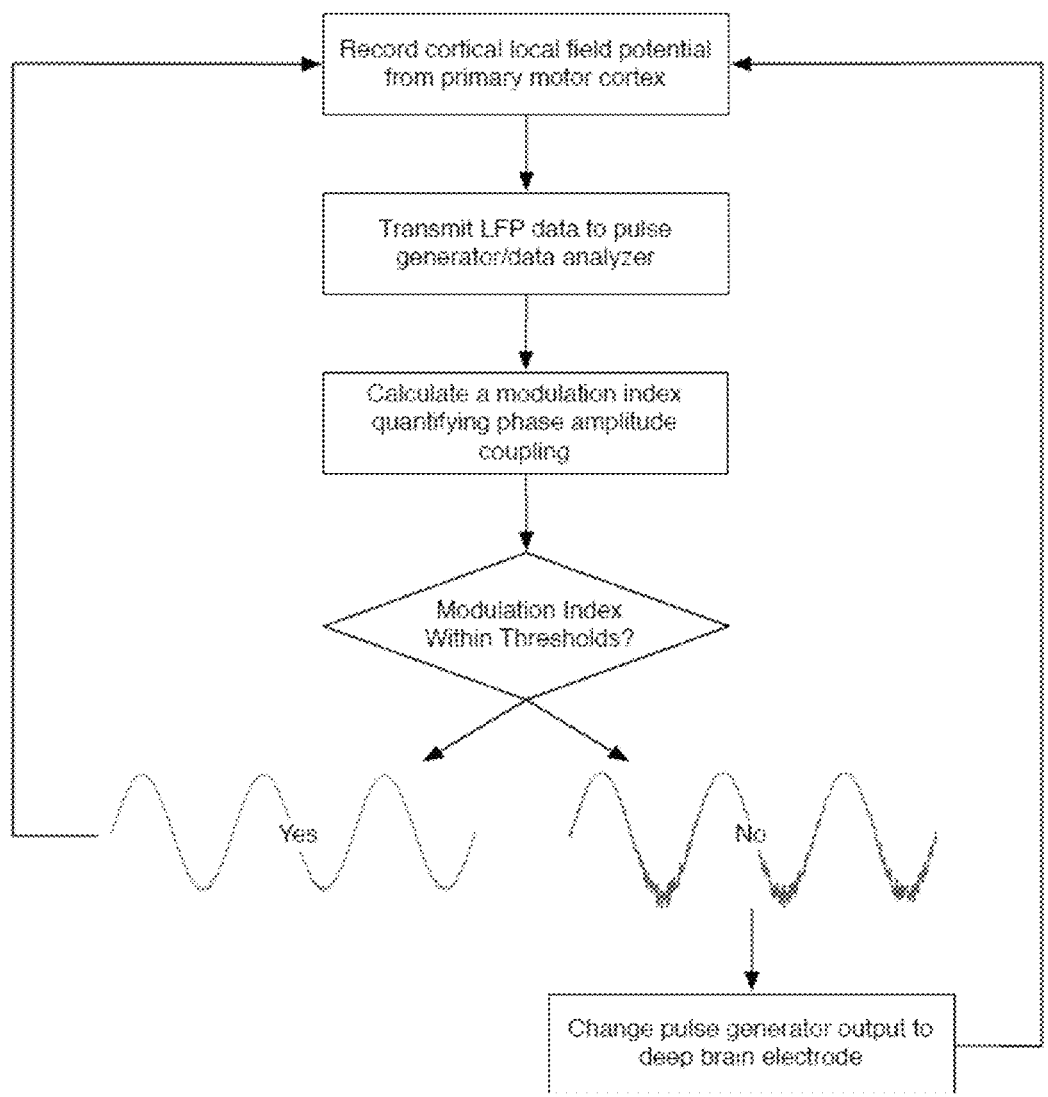
FIG. 1, Panels A-D show a block flowchart of embodiments of the present disclosure. Panel A: Flowchart of aspects of methods of the present disclosure. Panel B: Illustration of recording cortical local field potential (LFP) from a bipolar contact pair placed over the primary motor cortex of a subject's brain. Panel C: Illustration of raw LFP data. Panel D: Illustration of a deep brain stimulation electrode according to embodiments of the present disclosure.
Figure 1:
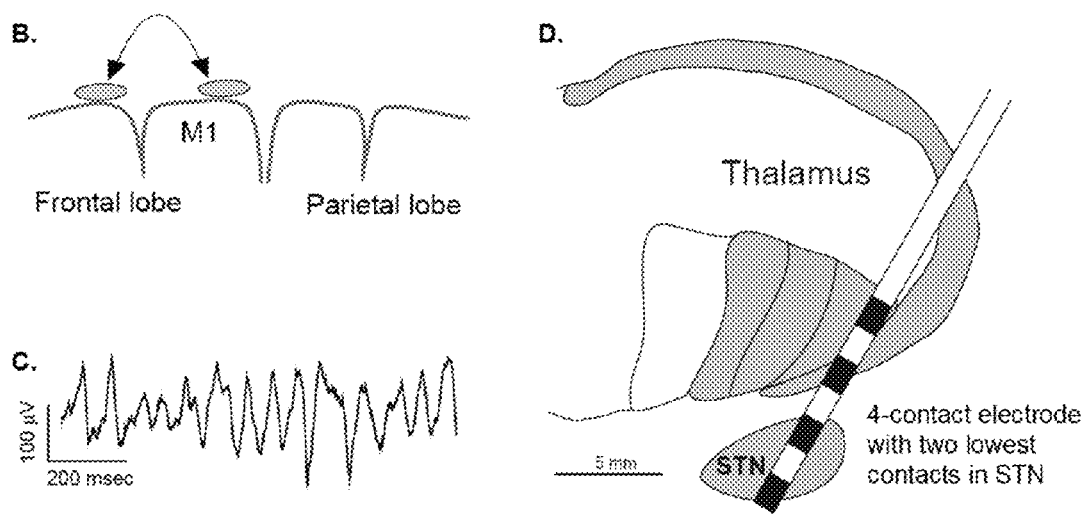

Aspects of embodiments of methods of the present disclosure are illustrated in FIG. 1, Panel A. In the embodiments illustrated in this figure, cortical local field potentials (LFPs) are recorded from the primary motor cortex of a subject. These cortical LFPs are then transmitted by any convenient means to a device, such as a pulse generator or data analyzer, that includes a processor. The device calculates a modulation index that quantifies the phase amplitude coupling of the LFPs. The calculated modulation index is then compared to thresholds (e.g., pre-defined thresholds, user-defined thresholds, patient-specific thresholds, etc.). If the calculated modulation index is within the thresholds, no further action steps are taken, and the cycle is repeated. If, however, the calculated modulation index is not within the thresholds, then deep brain stimulation is administered to the subject, via a pulse generator. In certain aspects, the pulse generator output is changed prior to administration of the deep brain stimulation to change one or more parameters of the stimulation (e.g., contact choice, amplitude, frequency, and the like), as shall be described more fully herein. The cycle may then be repeated in a manner effective to treat the subject for the neurological movement disorder.

FIG. 1, Panels B-D provide additional detail about the aforementioned embodiments. For instance, FIG. 1, Panel B is a non-limiting example of a manner of recording LFPs. In this illustration, the LFPs are recorded from a bipolar contact pair placed over the primary motor cortex of a subject's brain. The contacts may be nonpenetrating electrodes, as shall be described more fully below. Further, the location of the contacts may vary. In some embodiments, at least one electrode is located at a position corresponding to the arm area of primary motor cortex M1. Turning to FIG. 1, Panel C, an illustration of raw LFP data is presented. The raw LPF signal may be manipulated and/or processed in one or more ways prior to calculation of the modulation index, such as by filtering certain frequencies and/or amplitudes, altering the sampling rate, and the like. Turning to FIG. 1, Panel D, an illustration is presented of a deep brain stimulation electrode according to embodiments of the present disclosure. Such a deep brain stimulation electrode may stimulate a region of the subject's brain, such as the thalamus and/or basal ganglia.

In certain aspects, methods of the present disclosure may utilize one or more commercially available electrodes, devices, or systems. Methods of performing deep brain stimulation, and deep brain stimulation devices and/or systems of interest include, but are not limited to, those methods, devices, and/or systems described in U.S. Pat. Nos. 5,716,377; 5,843,148; 6,066,163; 6,253,109; 6,463,328; 6,484,059; 6,539,263; 6,587,724; 6,484,059; 6,920,359; 7,003,352; 7,033,326; 7,149,574; 7,151,961; 7,212,867; 7,295,880; 7,295,880; 7,346,382; 7,369,899; 7,539,543; 7,809,446; 7,904,134; and 7,957,808; the disclosures of which are each incorporated herein by reference.

Various aspects of embodiments of the methods shall now be described in greater detail below.

Recording Cortical Local Field Potentials

Aspects of embodiments of the subject methods involve recording local field potentials, such as cortical local field potentials. According to certain embodiments, recording local field potentials (e.g., cortical local field potentials) is carried out by electrocorticography (ECoG) or electroencephalography (EEG). In certain aspects, recording cortical local field potentials involve the use of an array (e.g., an electrocorticography array, such as a multi-contact electrocorticography strip). The LPF recording element may be a strip, such as a subdural electrocorticography strip. The LFP recording element may include a non-brain-penetrating electrode (e.g., an ECoG or EEG electrode), and in certain aspects may include only non-brain-penetrating electrodes.

The precise number of contacts (e.g., electrodes) contained in a strip may vary. In certain aspects, an electrocorticography strip may include one or more contacts, such as 2 or more, including 3 or more, e.g., about 3 to 6 contacts, about 6 to 12 contacts, about 12 to 18 contacts, about 18 to 24 contacts, about 24 to 30 contacts, about 30 to 48 contacts, about 48 to 72 contacts, about 72 to 96 contacts, or about 96 or more contacts. Where the array includes more than one contact, the contacts may be arranged into a regular repeating pattern (e.g., a grid, such as a grid with about 1 cm spacing between contacts), or no pattern. The contacts may be made of any convenient material for recording cortical local field potentials. In certain aspects, when EEG is used to measure the LFPs, the EEG electrodes may be held to the scalp with a cap.

The size of each contact may also vary depending upon such factors as the number of contacts in the strip, the location of the contact, the material, the neurological movement disorder, the age of the patient, and other factors. In certain aspects, a contact has a size (e.g., a diameter) of about 5 mm or less, such as about 4 mm or less, including about 3 mm, about 2 mm, about 1 mm, about 0.5 mm, or about 0.25 mm.

In certain embodiments, at least one contact is placed on the surface of a subject's brain so as to be placed in or on the primary motor cortex (M1). In certain aspects, two or more contacts are placed in or on M1, such as 2 or more, including 3 or more, e.g., about 3 to 5 contacts, about 5 to 8 contacts, or about 8 to 12 contacts. Embodiments include placing at least one contact in or on the arm area of M1, such as the posterior rim of motor cortex as illustrated in FIG. 13. In some aspects, this position may be about 3 cm from the midline, slightly medial to the "hand knob" as described in Yousry TA, et al. (1997) *Brain* 120 (Pt 1):141-157; the disclosure of which is incorporated herein by reference.

To facilitate placement of the at least one contact in a location, in certain aspects one or more markers (e.g., a radio-opaque marker) may be used. For instance, in certain aspects a marker, such as a radio-opaque marker, may be placed on the scalp over a desired location, such as the arm area of M1. A hole, such as a burr hole, may be made in the subject's scalp using any convenient means known in the art. In other aspects, a burr hole may already be present. For instance, a hole may already be present if already formed for deep brain stimulation lead placement. The hole may be used to advance the contact(s) to the desired location.

In certain aspects, an additional step may be performed to identify which contact(s) are closest to a desired location, such as M1. For example, contacts closest to M1 may be determined by anatomical and/or physiological methods, such as intraoperative CT merged to the preoperative MRI, allowing for the visualization of the central sulcus (see, e.g., FIG. 2, Panel A, and FIG. 12, Panel B) and the "hand knob" relative to the contacts, or lateral fluoroscopy on which the radio-opaque marker placed over M1 could be visualized. In other aspects, the closest contact to a location, such as M1, may also, or instead, be identified using nerve stimulation. For instance, the median nerve may be stimulated in order to generate a somatosensory evoked potential (frequency=2 Hz, pulse width=200 pee, pulse train length=160, amplitude 25-40 mAmp), with the closest electrode to M1 identified as the most posterior contact showing a negative N20 waveform.

Once contacts are placed, the LPFs may be recorded using any convenient means known in the art. In certain aspects, LFPs may be recorded using a recording system, such as a Guideline 4000 system (FHC Inc, Bowdoin, Me.) or an Alpha Omega Microguide Pro (Alpha Omega, Inc, Nazareth, Israel), and/or biosignal amplifiers, such as Synamps2 biosignal amplifiers (Neuroscan, El Paso, Tex.). The raw LFP signals may be sampled at any convenient rate, such as about 1000 Hz, about 1500 Hz, and the like, but should be greater than 200 Hz.

Recorded LFPs may be processed. Such processing may include applying one or more filters, such as a bandpass filter and/or a notch filter. Further, the sampling rate of the LFPs may be altered.

For example, in certain aspects processing may include applying a bandpass filter. A bandpass filter may separate the raw LFP data in about 2 to about 16 different frequency bands, or more. In certain embodiments, a bandpass filter may split a signal into about 2 frequency bands, about 4 frequency bands, about 6 frequency bands, about 8 frequency bands, about 10 frequency bands, about 12 frequency bands, about 14 frequency bands, about 16 frequency bands or more. Specific frequency bands may be selected to divide LFP data into physiologically important ranges. In some embodiments, a bandpass filter is employed to produce a signal including mu frequencies, beta frequencies, gamma frequencies, high gamma frequencies, or other ranges known to correspond to particular brain wave frequencies.

In certain aspects, one or more notch filters may be applied to the LFPs. A notch filter may be applied any frequency for which signal subtraction is desired. In certain embodiments, a notch filter may be used that filters frequencies at about 60 Hz, at about 120 Hz, or about 180 Hz. A notch filter may be applied to remove electrical hum or other noise, such as that from an A/C current. According to certain embodiments, independent component analysis may be used to remove artifacts caused by electrical hum, other noise, or artifact from the DBS stimulation. Independent component analysis can implemented using the EEGLAB toolbox (see Delorme & Makeig, J. Neurosci Methods (2004) 134(1):9-21). Independent component analysis was used for the EEG data in FIGS. 21 and 22.

In certain aspects, the sampling rate of LFPs may be altered using any convenient means, such as digitally. For instance, LFPs may be digitized at a sampling rate of about 200 samples per second or more, such as about 400 to 10000 samples per second, including about 400 to 2000 samples per second, about 400 to 1500 samples per second, or about 1000 samples per second.

Phase-Amplitude Coupling Indices

Embodiments of the subject methods include calculating a modulation index from the LFPs related to synchronization of brain circuits. In certain aspects, the modulation index may measure phase-amplitude coupling within M1.

In certain aspects, calculation of a modulation index includes calculating a Kullback-Liebler-based modulation index, a mean vector length modulation index, and/or applying a phase-amplitude coupling palette method.

For instance, in certain aspects calculation of a modulation index includes calculating a Kullback-Liebler (KL)-based modulation index. The KL-based modulation index method is described in Tort AB, et al. (2008) *Proc Natl Acad Sci USA* 105:20517-20522; the disclosure of which is incorporated herein by reference. Aspects of such a method may include filtering (e.g., bandpass filtering) LFPs. Any convenient means of bandpass filtering LFPs may be employed, such as bandpass filtering at low and high frequency using a two-way least squares FIR filter. A Hilbert transform may be applied, with the instantaneous phase and the instantaneous amplitude extracted from the low and the high frequency filtered signal, respectively. The entropy of the distribution of the instantaneous amplitude may then be computed for every 20° interval of the instantaneous phase and normalized by the maximum entropy value. In addition, for each frequency pair, the phase of the coupling ("preferred phase") may be calculated by determining the interval of the instantaneous phase at which the instantaneous amplitude was maximal.

In certain aspects, calculation of a modulation index includes calculating a mean vector length modulation index method. Such a method is described in Canolty R T, et al. (2006) *Science* 313:1626-1628; the disclosure of which is incorporated herein by reference. In certain aspects, such a method includes filtering the signals and extracting phase and amplitude, as described above. Next, a composite signal may be generated by combining the instantaneous phase of one frequency and the instantaneous amplitude of another frequency. The coupling may be quantified by computing the mean of this composite signal, where a larger mean indicates stronger phase-amplitude coupling. In certain aspects, the coupling may be quantified by calculating a phase locking value (PLV), where the amplitude signal is itself filtered at the same frequency as the phase signal, and the phase values of each are directly compared to give a phase locking value (see, e.g., Penny et al. (2008) J. Neurosci. Methods 174(1):50-61; and Cohen, M. X. (2008) J. Neurosci. Methods 168:494-499).

In both methods described above, the instantaneous phase and amplitude may be extracted from signals that are filtered. For instance, LFP signals may be filtered from, for example, about 1 Hz to about 1000 Hz, including from 4 to 50 Hz, 10 to 400 Hz, and the like. The step size may be about 0.5 Hz or greater, such as about 2 Hz, about 4 Hz, or about 6 Hz.

A calculated modulation index may, in certain aspects, be normalized. For example, a modulation index such as described above may be normalized to the mean and standard deviation of from 100 to 10,000 (e.g., 200) modulation indices computed from surrogate signals, where the surrogate signals are created by combining the instantaneous phase and amplitude with varying time lags. Accordingly, in certain aspects a modulation index may be computed for each frequency pair.

In certain aspects, calculation of a modulation index includes applying a phase-coupling palette method to compute the broadband gamma amplitude, such as that described in Miller K J, et al. (2009) *J Neurosci* 29:3132-3137 and Miller K J, et al. (2010) *Frontiers in Human Neuroscience* 4:197; the disclosures of which are incorporated herein by reference. The phase may be extracted from signals filtered at low frequency. Low frequency filtering may be achieved by any convenient method, such as by using the Morlet wavelet. The phase-amplitude coupling may then be computed by averaging the broadband gamma amplitude for each phase interval to generate a coupling diagram.

In certain aspects, calculation of a modulation index includes at least two of (i) calculating a Kullback-Liebler-based modulation index, (ii) calculating a mean vector length modulation index, (iii) applying a phase-amplitude coupling palette method; and/or (iv) calculating a phase-locking value. In certain aspects, all three may be calculated. In certain aspects, the indices may be combined, such as by using linear regression, nonlinear regression, weighted combination, and the like, to create a composite modulation index.

In certain aspects, methods of the present disclosure include determining the magnitude of the maximal coupling (MI max) and/or the frequencies involved in the maximal coupling (Fmax phase and Fmax amplitude). The overall magnitude (MI mean) of beta-broadband gamma coupling may be calculated, such as by averaging the coupling between phases extracted from the 13-30 Hz band and the amplitude extracted from the 50-250 Hz band.

The computed modulation index may be compared to a control value or range, such as a threshold range. In certain embodiments, the threshold range is based on control values (e.g., reference standards, values obtained from a control population, and the like) and/or may be tailored for a particular subject. The control population may comprise subjects that do not have the neurological movement disorder, and/or subjects who are asymptomatic for the neurological movement disorder. For a particular subject, a threshold range may stay constant over time, or may vary over time.

A threshold value and/or range may be predetermined. Any convenient means of setting a control value may be employed, such as a user interface (e.g., via controls, a graphical user interface on a display, and the like). The threshold range may be stored in a computer readable medium so that the computed modulation index may be compared, using a processor, to the threshold range.

Deep Brain Stimulation

Aspects of embodiments of the present disclosure include administration of deep brain stimulation. As described above, deep brain stimulation has been widely used and is well known in the art. Any convenient means of administering deep brain stimulation may be employed in practicing the subject methods.

In certain aspects, methods of the present disclosure involve placing one or more deep brain stimulation electrodes. Such surgical placement may be performed using any of a variety of methods known in the art, such as the approaches described in Starr P A, et al. (2002) *Journal of Neurosurgery* 97:370-387 and Ostrem J L, et al. (2011) *Neurology* 76:870-878; the disclosures of which are incorporated herein by reference. For example, an intended target location, such as a STN target location, may be identified as a T2 hypointensity immediately lateral to the anterior margin of the red nucleus and superior to the lateral part of the substantia nigra pars reticulata (generally close to 12 mm lateral, 3 mm posterior, and 4 mm inferior to AC-PC). Final adjustments on target coordinates may be made during the surgery based on identification of movement-related single cell discharge. A DBS lead (such as a model 3389, Medtronic, Inc., Minneapolis, Minn., USA) may be placed at these coordinates with the most ventral contact (contact 0) at the base of STN and contact 1 in the center of the motor territory of the STN. Targeting may be confirmed by evaluation of stimulation induced symptom improvement and adverse effects, as well as by visualization of DBS lead location on an intraoperative CT scan as described in Shahlaie K, et al. (2011) *Neurosurgery* 68:114-124; the disclosure of which is incorporated herein by reference. An additional postoperative MRI may be used to confirm the correct placement of DBS leads in each patient (see, e.g., FIG. 2, Panel C).

Once placed, the effects of STN deep brain stimulation may be tested. In certain aspects, testing may include recording cortical LFPs while patients were in the rest state. STN may be stimulated according to methods and parameters known in the art, such as via a Medtronic model 3389 DBS lead at 4 Volts, 60 μs and 180 Hz in bipolar mode using contacts 1 negative and 2 positive.

Administration of a Pharmacological Agent

Embodiments may also include administration of an effective amount of at least one pharmacological agent. By "effective amount" is meant a dosage sufficient to prevent or treat a neurological movement disorder in a subject as desired. The effective amount will vary somewhat from subject to subject, and may depend upon factors such as the age and physical condition of the subject, severity of the neurological movement disorder being treated, the duration of the treatment, the nature of any concurrent treatment, the form of the agent, the pharmaceutically acceptable carrier used if any, the route and method of delivery, and analogous factors within the knowledge and expertise of those skilled in the art. Appropriate dosages may be determined in accordance with routine pharmacological procedures known to those skilled in the art, as described in greater detail below.

If a pharmacological approach is employed in the treatment of a neurological movement disorder, the specific nature and dosing schedule of the agent will vary depending on the particular nature of the disorder to be treated. Representative pharmacological agents that may find use in certain embodiments of the subject invention include, but are not limited to, levodopa, carbidopa, catechol O-methyltransferase inibitors, monoamine oxidase inhibitors, dopamine agonists, anticholinergics, catecholamines, baclofen, benzodiasepines, tetrabenezine, diazepam, clonazepam, lorazepam, and the like.

In certain aspects, the administration of a pharmacological agent involves using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

Changing Parameters of Administration of Deep Brain Stimulation

In certain embodiments of the subject methods, if a calculated modulation index is outside of a threshold value or range, one or more parameters of a deep brain stimulation and/or administration of a pharmacological agent may be changed. Accordingly, the subject methods may be performed using suitable computing means such as suitable hardware/software for performing the subject methods.

In certain embodiments, programming may control a device to administer a deep brain stimulation and/or a pharmacological agent to a subject, e.g., programming may be configured to determine suitable amplitude, frequency, intensity, dosage, etc. In certain embodiments programming may control a device to administer deep brain stimulation to a subject, e.g., may control the activation/termination of a pulse generator device including selecting suitable parameters. Such programming may be configured to, or otherwise be capable of, directing a microprocessor to activate, i.e., turn "on" and "off" a deep brain stimulation applying device for applying deep brain stimulation to a subject. For example, if so determined, the processor may direct the deep brain stimulation applying device to provide the appropriate deep brain stimulation to result in the desired action.

Accordingly, a processor may select the appropriate parameters (e.g., frequency, intensity, duration, etc.) depending on what is required and direct a deep brain stimulation applying device and/or a drug delivery device to implement the parameters.

Thus in certain aspects, the subject methods operate as a closed-loop control system which may automatically adjust one or more parameters in response to a calculated modulation index or condition of a subject. Under a closed-loop feedback system to provide automatic adjustment of parameters, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

Devices

As described above, the present disclosure also provides devices which may find utility in practicing the subject methods. Devices of the present disclosure may be employed to carry out one or any combination of steps of the methods of the present disclosure according to any embodiment as described above in the section entitled "Methods", which description is incorporated herein. According to certain embodiments, the devices include a computer-readable medium having instructions for carrying out any aspect of the methods of the present disclosure. The instructions may be executed by a processor. In certain aspects, devices of the present disclosure include an input configured to receive cortical local field potentials (LFPs) from at least one electrode; an output configured to be in electronic communication with a pulse generator for administering deep brain stimulation; a processor in electronic communication with the input and the output, the processor programmed to: calculate a modulation index from the LFPs received from the input; and change at least one parameter of the pulse generator based at least in part on the value of the modulation index. Such input(s) and/or output(s) may include standard connections known in the art.

The processor may be programmed to perform a subject method, and thus may be programmed to perform one or more actions such as calculating a modulation index, filtering LFPs, changing one or more parameters, and the like, as described above.

A great many variations of the subject devices may be employed. For example, in certain aspects a subject device includes a display, such as an LCD display, e-ink display, and the like. The display may include a user interface (e.g., a graphical user interface) that is in communication with the processor. The user interface may be used to set one or more parameters by the subject, or by a non-subject such as a doctor, nurse, or other caregiver. For example, the user interface may be used to set initial parameters for the pulse generator, to set the threshold values for the computed modulation index, and the like.

In certain aspects, the device may require a user intervention before taking one or more actions. For example, in certain embodiments the processor is programmed to require a user intervention via the user interface before changing at least one parameter of the pulse generator. The user intervention may be made via any convenient means, such as by the user interface of the device.

Aspects of embodiments of subject devices include a data logging element. The data logging element is in communication with the processor, and configured to non-transiently record at least the modulation index and the at least one parameter of the pulse generator. The data logging element may, in certain aspects, further record other parameters.

In certain aspects, a device may include an output that is configured to be in electronic communication with a drug delivery device configured to administer a pharmacological agent to a subject. In such devices, the processor may be programmed to change at least one parameter of the drug delivery device based at least in part on the value of the modulation index. The specific type of drug delivery device may itself vary, with pharmacological delivery devices of interest including, but not limited to, pumps (implantable or external devices), epidural injectors, syringes or other injection apparatus, catheter and/or reservoir operatively associated with a catheter, etc.

Devices may be configured to operate as a closed-loop device which may automatically adjust one or more parameters in response to a calculated modulation index or condition of a subject. For the closed-loop feedback device to provide automatic adjustment of parameters, a sensor (e.g., one or more electrodes, such as one or more ECoG or EEG electrodes) that senses a condition of the body (e.g., phase-amplitude coupling (PAC)) may be utilized. More detailed descriptions of devices and systems that may be employed in the practice of the present disclosure, and other examples of devices and feedback control techniques that may be employed are disclosed in U.S. Pat. No. 5,716,377, which is incorporated herein by reference.

Systems

Also provided by the present disclosure are systems for treating neurological movement disorders. Systems of the present disclosure may be employed to carry out one or any combination of steps of the methods of the present disclosure according to any embodiment as described above in the section entitled "Methods", which description is incorporated herein. According to certain embodiments, the devices include a computer-readable medium having instructions for carrying out any aspect of the methods of the present disclosure. The instructions may be executed by a processor. In certain aspects, systems include a pulse generator configured to administer deep brain stimulation to the subject; a subdural electrode adapted to record cortical local field potentials (LFPs) from a surface of the primary motor cortex of the subject; and a data analyzer in electronic communication with the pulse generator and the subdural electrode, the data analyzer comprising: a processor programmed to calculate a modulation index for synchronization of brain rhythms in the LFPs; and administer deep brain stimulation to the subject via the pulse generator if the calculated modulation index is outside of a predefined threshold range.

Accordingly, in certain aspects systems of the present disclosure may be computer-based systems. A "computer-based system" refers to the hardware, software, and data storage devices used to analyze the information of the present invention. The minimum hardware of embodiments of the computer-based systems includes a central processing unit (CPU) (e.g., a processor), an input device, an output device, and data storage device. Any one of the currently available computer-based systems may be suitable for use in the embodiments disclosed herein. The data storage device may include any manufacture including a recording of the present information as described above, or a memory access means that can access such a manufacture. For example, embodiments of the subject systems may include the following components: (a) a communications module for facilitating information transfer between the system and one or more users, e.g., via a user computer or workstation; and (b) a processing module for performing one or more tasks involved in the calculation of a modulation index.

Systems may be configured to operate as a closed-loop system which may automatically adjust one or more parameters in response to a calculated modulation index or condition of a subject. For the closed-loop feedback system to provide automatic adjustment of parameters, a sensor (e.g., one or more electrodes, such as one or more ECoG or EEG electrodes) that senses a condition of the body (e.g., phase-amplitude coupling (PAC)) may be utilized. More detailed descriptions of systems and devices that may be employed in the practice of the present disclosure, and other examples of systems and feedback control techniques that may be employed are disclosed in U.S. Pat. No. 5,716,377, which is incorporated herein by reference.

Embodiments of systems of the present disclosure include a drug delivery device, such as described above, in electronic communication with the processor and configured to administer a pharmacological agent to a subject. In such systems, the processor is further programmed to administer the pharmacological agent to the subject via the drug delivery device if the calculated modulation index is outside of the predefined threshold range.

Additionally, systems of the present disclosure may include a number of additional components, such as data output devices, e.g., monitors, printers, and/or speakers, data input devices, e.g., interface ports, a keyboard, a mouse, etc., fluid handling components, power sources, etc.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a deep brain stimulation and/or a pharmacological agent to a subject, e.g., programming may be configured to determine suitable amplitude, frequency, intensity, dosage, etc. In certain embodiments programming may control a device to administer deep brain stimulation to a subject, e.g., may control the activation/termination of a pulse generator device including selecting suitable parameters. Programming may be configured to, or otherwise be capable of, directing a microprocessor to activate, i.e., turn "on" and "off" a deep brain stimulation applying device for applying deep brain stimulation to a subject. For example, if so determined, the processor may direct the deep brain stimulation applying device to provide the appropriate deep brain stimulation to result in the desired action. Accordingly, a processor may select the appropriate parameters (e.g., frequency, intensity, duration, etc.) depending on what is required and direct a deep brain stimulation applying device and/or a drug delivery device to implement the parameters.

Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include one or more devices or systems, as described above, and/or pharmacological agents, as described above.

The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as described above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrode, etc.

The subject kits may also include a deep brain stimulation applying device, as described above. The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. flash drive, CD-ROM or DVD-ROM, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

Utility

The subject methods, devices, systems and kits find use in a variety of applications in which it is desired to treat a subject for a condition, e.g., a neurological movement disorder; to reduce the abnormal motor signs of a condition (e.g., clinical disability associated with a movement disorder); and/or to maintain the state of a subject. Specific neurological movement disorders of interest include, but are not limited to, Parkinson's disease, and primary and secondary dystonias, Huntington's disease, essential tremor, mood disorders, psychotic disorders, and other psychiatric conditions.

The subject methods may be applied to a variety of subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects") such as, but not limited to, birds, mice, rats, dogs, cats, livestock and horses. Accordingly, it is to be understood that any subject in need of treatment for a condition according to the present disclosure is suitable.

Moreover, suitable subjects include those who have and those who have not been diagnosed with a neurological movement disorder. In certain embodiments, the subject methods may include a diagnostic step. Individuals may be diagnosed as being in need of the subject methods using any convenient protocol suitable for use in diagnosing the presence of a neurological movement disorder, such as visual diagnosis, physical testing, neurological exam, blood and/or urine testing, electrical recording (e.g., electromyography or electroencephalography), genetic testing, imaging (e.g., CT scan, MRI scan, and/or PET scan), and the like. In addition, individuals may be known to be in need of the subject methods, e.g., they are exhibiting one or more clinical presentations of a neurological movement disorder.

Methods of determining the neurological state of a subject are known to those of skill in the art (such as by using diagnosis protocols, e.g., as described above). A subject's neurological state may be understood to refer to the presence or absence of one or more neurological movement disorders, e.g. the absence of midstage PD that is no longer optimally improved by medication, and/or the absence of clinical presentations of a neurological movement disorders. Accordingly, the phrase "maintaining the neurological state" of a subject refers to the preservation or the subject's existing state (e.g., the subject does not develop one or more new neurological movement disorders if the subject does not already have the condition; the subject does not start to exhibit new clinical presentations of a neurological movement disorder; etc.).

Methods of the present disclosure may further include assessing the efficacy of a treatment protocol, which may be performed using any convenient protocol, e.g., by monitoring the rate of improvement of a neurological movement disorder (such as by using the diagnosis protocols, e.g., as described above).

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Materials and Methods

The following are general materials and protocols used in the Examples 1-6 below.

Patients

Twenty-five subjects with movement disorders were recruited from the movement disorders surgery clinics at the University of California, San Francisco (UCSF) or the San Francisco Veteran's Affairs Medical Center (SFVAMC). Motor impairment was quantified within 30 days prior to surgery using the Unified Parkinson's Disease Rating Scale part III (UPDRS-III) in the off and on medication state (16 PD subjects), or Toronto Western Spasmodic Torticollis Rating Scale (TWSTRS) (9 dystonia patients). Inclusion criteria were: 1) PD patients, akinesia and rigidity as the most prominent symptoms, UPDRS III between 30 and 50 in the off state; or 2) primary dystonia patients with predominantly cervical or cranio-cervical dystonia and without prominent arm involvement.

To provide a comparison group of humans without basal ganglia disease, subjects with medically intractable epilepsy were studied, recruited from the invasive epilepsy monitoring units at UCSF and the University of Washington Medical Center (UWMC). Only epilepsy patients with subdural grid arrays covering perirolandic cortex were included. Studies were approved by the institutional ethics committees and were in agreement with the Declaration of Helsinki. All patients gave their written informed consent to participate.

ECoG Strip and Grid Location

To record cortical local field potentials in patients with movement disorders, a multi-contact subdural electrocorticography strip was placed on the surface of the brain with at least one contact covering the primary motor cortex (M1). In certain trials, a 6-contact subdural electrocorticography strip (3 mm contacts, 1 cm spacing, Ad-Tech, Racine, Wis.) was placed on the surface of the brain with one contact covering the primary motor cortex (M1). In other trials, a 28-contact subdural electrocorticography strip (2×14, 28-contact single tail grid comprising 2 mm contacts, 1 cm spacing; Ad-Tech, Racine, Wis.) was placed on the surface of the brain with at least one contact covering M1 (see, e.g., FIG. 12, Panels A-B).

The intended target location was the arm area of M1, 3 cm from the midline, slightly medial to the "hand knob" as described in Yousry TA, et al. (1997) *Brain* 120 (Pt 1):141-157; the disclosure of which is incorporated herein by reference. A radio-opaque marker was placed on the scalp over this location. The ECoG strip was then advanced through the burr hole used for the DBS lead placement in the direction of the marker. For patients with epilepsy, cortical activity was recorded using 8×8 contact subdural electrode grids (4 mm contacts, 1 cm spacing, Ad-Tech, Racine, Wis.; Integra, Plainsboro, N.J.) placed over the cortex to localize the seizure foci.

The contacts closest to M1 were determined using anatomical and/or physiological methods. For movement disorder patients, electrode localization was determined using either the intraoperative CT merged to the preoperative MRI, allowing for the visualization of the central sulcus (FIG. 2, Panel A, and FIG. 12, Panel B) and the "hand knob" relative to the contacts, or lateral fluoroscopy on which the radio-opaque marker placed over M1 could be visualized. For patients with epilepsy, a postoperative CT was merged to the preoperative MRI allowing for the determination of the electrode position by visualization of the sulcus or by using the CTMR package described in Hermes D, et al. (2010) *J Neurosci Methods* 185:293-298; the disclosure of which is incorporated herein by reference. See, e.g., FIG. 2, Panel B. In addition, the median nerve was stimulated in order to generate a somatosensory evoked potential (frequency=2 Hz, pulse width=200 μsec, pulse train length=160, amplitude 25-40 mAmp). The closest electrode to M1 was defined as the most posterior contact showing a negative N20 waveform.

DBS Electrode Implantation in PD and Dystonia Patients

Figure 2:
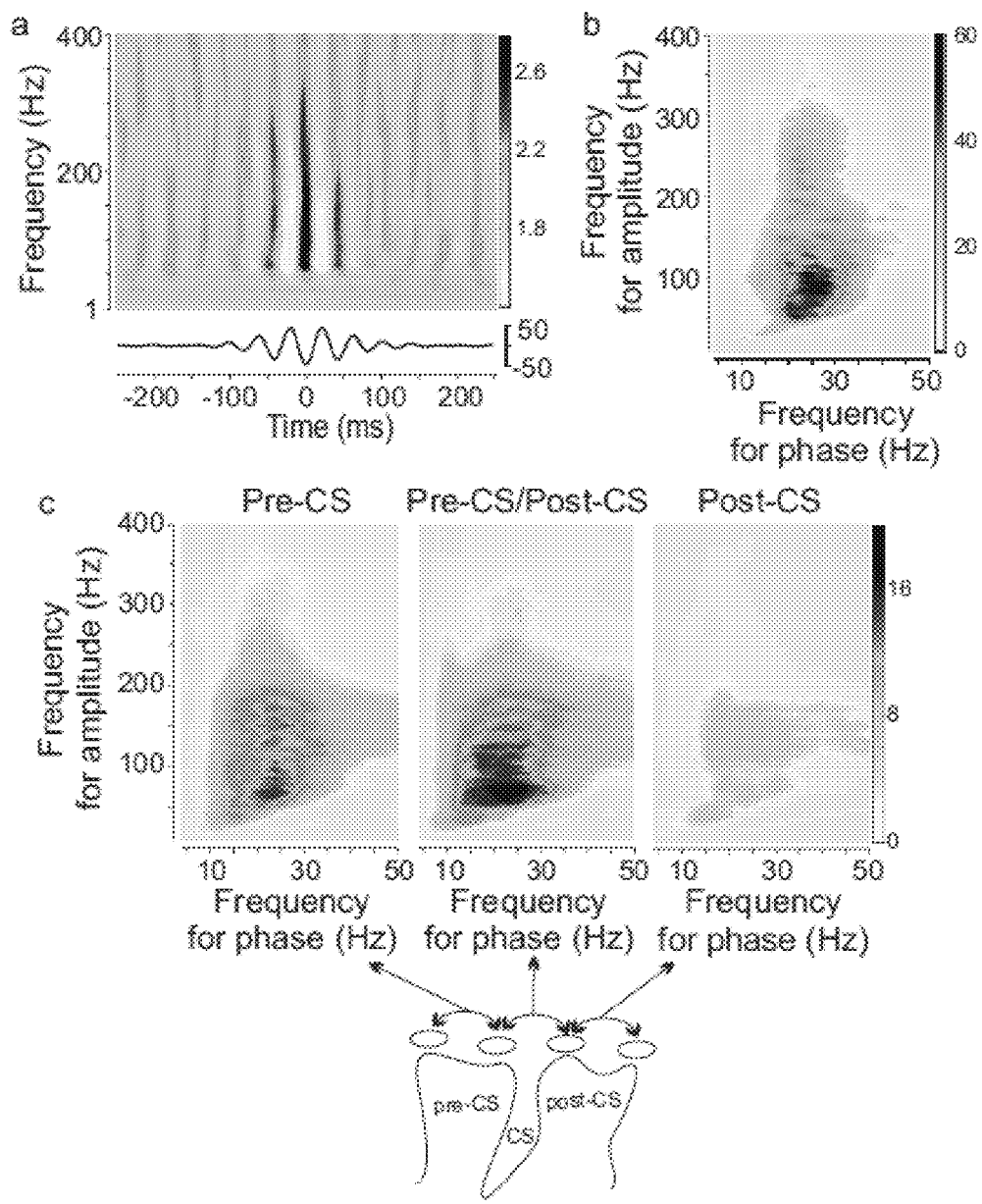
FIG. 2, Panels A-C show phase-amplitude coupling observed in the cortex of PD patients in the alert rest state and the spatial localization of this coupling. Panel A: Scalogram aligned on the beta trough. M1 LFP signals were filtered at different frequencies and aligned on the trough of the beta rhythm (13-30 Hz, lower part of the panel). Panel B: Modulation indices over a range of frequencies for phase and amplitude showing a strong coupling between the phase of the beta rhythm and the amplitude of gamma activity (50-300 Hz). The darkest colors represent the strongest coupling. Panel C: Spatial localization of strong phase-amplitude coupling. Each plot shows the averaged modulation indices across all PD patients for particular electrode pairs. Left, both electrodes anterior to the central sulcus (pre-CS). Middle, electrode pair crossing the central sulcus (CS). Right, both electrodes located posterior to the central sulcus (post-CS). Schematic representation of the electrode localization relative to the central sulcus is shown on the lower part of the panel.

Planning and surgical placement of deep brain stimulation electrodes in the STN were performed using methods described in Starr P A, et al. (2002) *Journal of Neurosurgery* 97:370-387 and Ostrem J L, et al. (2011) *Neurology* 76:870-878; the disclosures of which are incorporated herein by reference. Briefly, the intended STN target location was identified as a T2 hypointensity immediately lateral to the anterior margin of the red nucleus and superior to the lateral part of the substantianigra pars reticulata (generally close to 12 mm lateral, 3 mm posterior, and 4 mm inferior to AC-PC). Final adjustments on the target coordinates were made during the surgery based on identification of movement-related single cell discharge. A DBS lead (model 3389, Medtronic, Inc., Minneapolis, Minn., USA) was then placed at these coordinates with the most ventral contact (contact 0) at the base of STN and contact 1 in the center of the motor territory of the STN. Targeting was confirmed by evaluation of stimulation induced symptom improvement and adverse effects, as well as by visualization of DBS lead location on an intraoperative CT scan as described in Shahlaie K, et al. (2011) *Neurosurgery* 68:114-124; the disclosure of which is incorporated herein by reference. An additional postoperative MRI was used to confirm the correct placement of DBS leads in each patient (FIG. 2, Panel C).

Cortical and STN LFP Recordings

In PD and dystonia patients, cortical and subthalamic nucleus LFPs were recorded intra-operatively, immediately following DBS electrode implantation. All antiparkinsonian and antidystonic medications were stopped 12 hours before the start of surgery. Although propofol was used for the initial surgical exposure, recordings were performed at least 30 minutes after stopping propofol. This is sufficient time for all neuronal effects of this agent to be eliminated. In epilepsy patients cortical LFPs were recorded 4-6 days after grid implantation.

LFPs of PD and dystonia patients were recorded using customized clinical recording systems, the Guideline 4000 system (FHC Inc, Bowdoin, Me.) (20 subjects) or the Alpha Omega Microguide Pro (Alpha Omega, Inc, Nazareth, Israel) (5 subjects) and sampled at 1000 Hz and 1500 Hz, respectively. Bipolar STN LFPs were recorded from contact 1 (active) and 2 (reference) of the DBS electrode using a clip attached to the guide tube as the ground. Due to technical issues, STN LFPs of 1 PD patient and 2 dystonia patients were unavailable. Cortical LFPs were recorded from the five most posterior contacts (contacts 1-5) referenced to the most anterior (contact 6). A needle electrode in the scalp served as the ground. Signals were bandpass filtered 1-500 Hz, amplified×7000.

Cortical LFPs of epilepsy patients from UWMC were recorded with Synamps2 biosignal amplifiers (Neuroscan, El Paso, Tex.). Signals were bandpass filtered from 0.15 to 200 Hz and sampled at 1000 Hz, with respect to a scalp reference and ground. Two epilepsy patients were studied at UCSF using either the Guideline 4000 system or a Nicolet video-ECoG recording system. Cortical LFPs were bandpass filtered from 1 to 500 Hz and sampled at 1000 Hz.

Behavioral Paradigms

Cortical LFPs were recorded in two behavioral conditions. In the first condition, 'rest,' patients were instructed to relax with eyes open, fixating on a point approximately 1 meter away, for at least 30 seconds. In the second condition, 'movement task,' patients performed an alternating stop/move task during which they were verbally asked to move the arm for 3-5 s (flexion-extension of the elbow) and to stop the movement for 3-5 s. All patients were tested in the 'rest' conditions. All PD, dystonia and two epilepsy patients were tested in the 'movement task'. Muscle activity was recorded using surface electromyography (EMG) from contralateral anterior deltoid, biceps brachii, extensor carpi radialis (bandpass filter 20-1000 Hz, amplification×7000, sampling rate 1 KHz or 1.5 KHz) and accelerometer. All subject were asked to move slowly, such that movement velocities across all patient groups were similar ($p > 0.05$).

Deep Brain Stimulation

To investigate the effect of STN deep brain stimulation, cortical LFPs were recorded while patients were in the rest state. STN was stimulated through the Medtronic model 3389 DBS lead at 4 Volts, 60 μs and 180 Hz in bipolar mode using contacts 1 negative and 2 positive.

Signal Processing

A bipolar montage between adjacent contacts was used in order to obtain a better spatial localization and reduced noise (C1-C2; C2-C3 . . . ). Line frequency noise was rejected by applying a notch filter between 58-62 Hz using a 3rd-order Butterworth filter. Thirty seconds of continuous recording were used for the analyses. For analyses LFPs recorded at 1500 Hz were downsampled to 1K. All analyses were performed using Matlab 7.10 software (Mathworks).

Time-frequency analysis was performed to visualize the modulation of M1 power time locked to the beta trough. Beta troughs were identified by extracting the phase of M1 or STN LFPs filtered in beta band (13-30 Hz) and by taking the minima of that signal. The ECoG power was then extracted from M1 LFPs filtered at different frequencies using the eegfilt (1-400 Hz in steps of 1 Hz, eegfilt.m from the EEGLAB toolbox), normalized and aligned on the beta trough. For each patient, the time at which the strongest cortical modulation occurred relative to the beta trough was determined using the time triggered spectrogram.

Power spectral density (PSD) was calculated using the Welch periodogram method, (Matlab function pwelch). The "peak power" was defined as the maximum PSD value between 13 and 30 Hz and the "beta log power" was defined as the average of the log PSD between 13 and 30 Hz.

Magnitude squared coherence was used to study the relationship between STN LFPs and M1 LFPs (Matlab function mscohere), and Fisher transformed by taking the inverse hyperbolic tangent. For PSD and coherence calculations a Fast Fourier transform of 513 points (for a frequency resolution of 1.95 Hz) and 50% overlap was used, using a Hanning window to reduce edge effects.

Phase-Amplitude Coupling Indices

Phase-amplitude coupling within M1 (all subjects), within STN (PD and dystonia subjects) and between those two structures (PD and dystonia subjects) was investigated. In this last condition, the phase was extracted from STN LFPs while the amplitude was extracted from M1 LFPs and vice versa. Interactions between the phase of low frequency signal and the amplitude of high frequency signal were investigated using three different methods that have been previously used to investigate phase-amplitude coupling.

In the "Kullback-Liebler (KL)-based modulation index" method, LFPs were bandpass filtered at low and high frequency using a two-way least squares FIR filter. The Hilbert transform was applied and the instantaneous phase and the instantaneous amplitude were extracted from the low and the high frequency filtered signal, respectively. The entropy of the distribution of the instantaneous amplitude was then computed for every 20° interval of the instantaneous phase and normalized by the maximum entropy value. In addition, for each frequency pair, the phase of the coupling ("preferred phase") was calculated by determining the interval of the instantaneous phase at which the instantaneous amplitude was maximal. The KL-based modulation index method is described in Tort A B, et al. (2008) *Proc Natl Acad Sci USA* 105:20517-20522; the disclosure of which is incorporated herein by reference.

For the "mean vector length modulation index" method, after filtering the signals and extracting the phase and amplitude, as described above, a composite signal was generated by combining the instantaneous phase of one frequency and the instantaneous amplitude of another frequency. The coupling was quantified by computing the mean of this composite signal. A larger mean indicates stronger phase-amplitude coupling. The mean vector length modulation index method is described in Canolty R T, et al. (2006) *Science* 313:1626-1628; the disclosure of which is incorporated herein by reference.

In both methods described above, the instantaneous phase and amplitude were extracted from signals filtered from 4 to 50 Hz in steps of 2 Hz and from 10 to 400 in steps of 4 Hz, respectively. Then the index was normalized to the mean and standard deviation of 200 modulation indices computed from surrogate signals. The surrogate signals were created by combining the instantaneous phase and amplitude with varying time lags. A modulation index was computed for each frequency pair and all values were represented on a color z-score scale plot. Statistical significance threshold was determined after Bonferroni correction for multiple comparisons (z=4.5).

The "phase-coupling palette" method used a "decoupling method" to compute the broadband gamma amplitude, as described in Miller K J, et al. (2009) *J Neurosci* 29:3132-3137 and Miller K J, et al. (2010) *Frontiers in Human Neuroscience* 4:197; the disclosures of which are incorporated herein by reference. The phase was extracted from signals filtered at low frequency using the Morlet wavelet to 50 Hz in steps of 1 Hz. The phase-amplitude coupling was then computed by averaging the broadband gamma amplitude for each of the 24 phase intervals and used to generate a coupling diagram ("palette"). In order to determine the significance of the coupling, the 30 s of recordings were broken into smaller epochs (1 s). For each epoch, the magnitude of the phase-amplitude coupling was calculated by averaging the broadband gamma amplitude for each of the 24 phase intervals. A coupling vector was determined for each epoch by combining the phase interval (vector angle) and the broadband gamma amplitude during that phase interval (vector length). In addition, the phase at which the maximal coupling occurred (preferred phase) was determined by taking the angle of the averaged coupling vector.

For each method of quantifying phase-amplitude coupling, the magnitude of the maximal coupling (MI max) and the frequencies involved in the maximal coupling (Fmax phase and Fmax amplitude) were determined. The overall magnitude (MI mean) of beta-broadband gamma coupling for each subject was also calculated by averaging the coupling between phases extracted from the 13-30 Hz band and the amplitude extracted from the 50-250 Hz band. Using the KL-based modulation index method, the 'Beta preferred phase' was computed by averaging the phases at which the maximal coupling occurred, between phases extracted from the 13-30 Hz band and the amplitudes extracted from the 50-250 Hz band (circ_mean.m from the circular statistics toolbox).

Statistical Analyses

Statistical analyses were performed in SPSS and Matlab. Given the non-normal distribution of calculated indices, non-parametric tests were used (Kruskal-Wallis, circular Kruskal-Wallis, Kolmogorov-Smirnov test and Rayleigh test) to evaluate statistical differences between the three disease groups. For statistical comparisons of phase-amplitude coupling modulation indices between patient groups (FIG. 3, Panels B and D; and FIG. 4, Panel D), a mean beta phase-broadband gamma modulation index for each individual subject was calculated by averaging all modulation indices (Kullback-Liebler method, described above) within the frequency range 13-30 Hz (phase) and 50-250 Hz (amplitude). This range is shown within the dotted box in FIG. 3, Panel A. Patient groups were then summarized by the median and range of the individual subjects' mean beta phase-broadband gamma modulation indices.

Example 1

Characteristics of Cortical Phase-Amplitude Coupling in Pd

As described above, 25 subjects with movement disorders (16 PD, 9 primary cranio-cervical dystonia) undergoing STN deep brain stimulator placement, and 9 subjects with epilepsy undergoing invasive monitoring with implanted subcortical grids, were studied. Cortical LFPs were recorded in all subjects, and STN LFPs were recorded in 15 PD subjects and 7 of 9 dystonia subjects. In all cases, the subdural electrodes covered the arm area of sensorimotor cortex (FIG. 7, Panels A-B).

FIG. 2, Panel A shows an example of the relationship between beta phase and broadband gamma M1 LFP amplitude for an individual PD patient in an alert resting state (patient PD 8). M1 LFP signals were filtered at different frequencies and aligned on the trough of the beta rhythm (13-30 Hz). Visual inspection of this time-frequency plot revealed an increase in broadband gamma power at the trough of the beta oscillation. Phase modulation of signal amplitude was seen over amplitude frequencies from 40 to 400 Hz.

FIG. 2, Panel B shows a plot of an index of the magnitude of M1 phase-amplitude coupling computed for the same PD patient over a broad range for frequencies for phase and frequencies for amplitude (using the Kullback-Liebler (KL)-based modulation index; in this plot the value of each (x,y) coordinate represents the strength of coupling between the phase of the x frequency and the amplitude of the y frequency. A strong interaction between the phase of the beta rhythm, especially between 20-30 Hz in this example, and the amplitude of gamma activity (50-300 Hz) can be observed (darkest color on each graph). Similar patterns of significant cross frequency coupling (z-score>4.5 for at least one combination of phase and amplitude) were observed in all PD patients. The strongest modulation was always observed between 50 and 250 Hz. To investigate the cortical localization of coupling, composite modulation index plots were constructed for three contact pairs selected based on their positions relative to central sulcus (CS); the "pre-CS", "CS" and "post-CS" pairs. The plots show the average modulation index at each frequency across all PD subjects (FIG. 2, Panel C). Phase-amplitude coupling was the strongest for electrode pairs that have at least one contact over the precentral gyrus. For subsequent grouped analyses in FIG. 3, Panels A-D and FIG. 4, Panels A-D, either the pre-CS or the CS contact pairs were used, depending on which of the two showed the highest phase-amplitude coupling.

Example 2

Motor Cortex Phase-Amplitude Coupling is Exaggerated in PD

Figure 3:
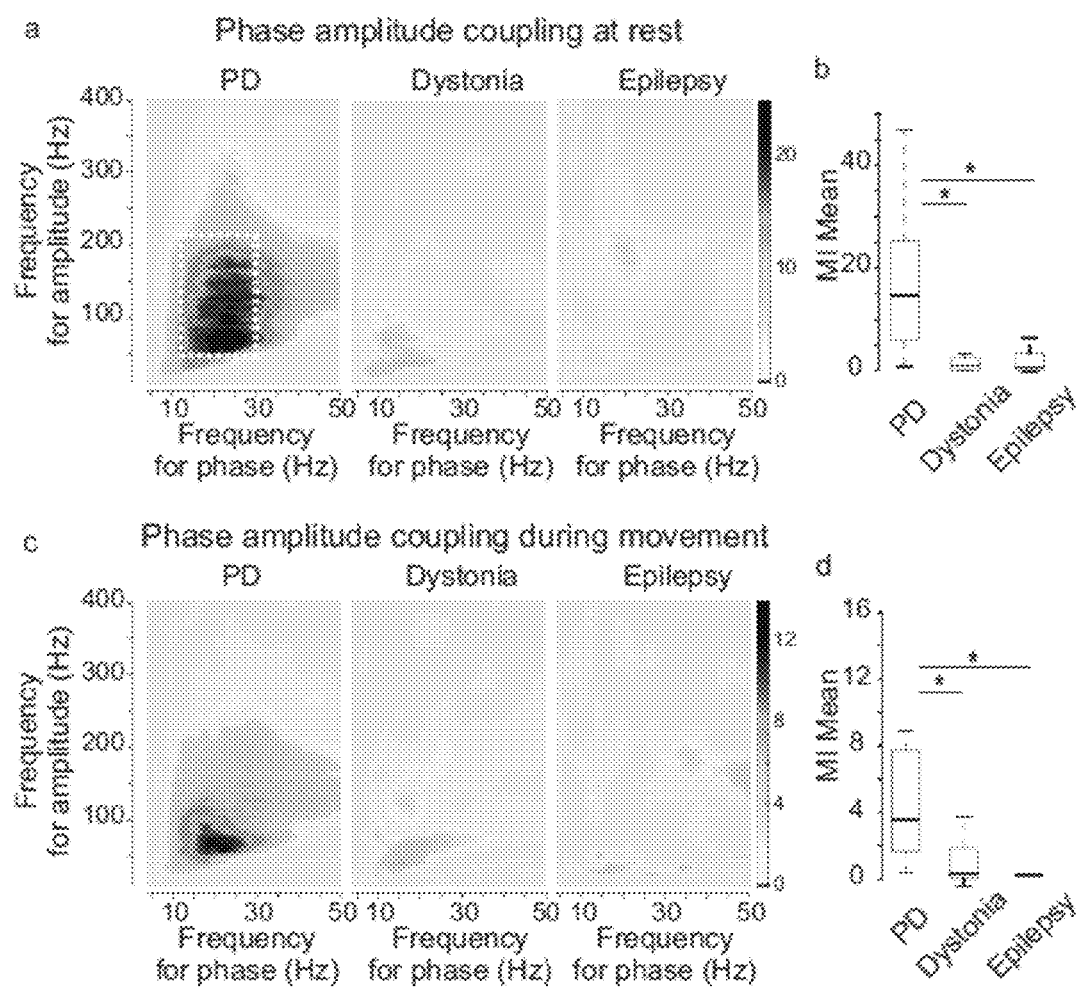
FIG. 3, Panels A-D depict a comparison of phase-amplitude coupling in the three different disease states. Panel A: Subjects in a state of alert rest. Each plot shows the averaged modulation indices across all patients with the same disease. The white dotted box (left panel) shows the range of frequencies over which the individual subject modulation indices are averaged to generate the statistical comparisons between groups (MI mean.

Averaged M1 modulation index plots for all patients in each disease group, in the alert resting state, are shown in FIG. 3, Panel A. For statistical comparison between groups, the modulation index of each patient was averaged across the beta band (frequency for phase 13-30 Hz; frequency for amplitude 50-250 Hz. The range of frequencies used in averaging is indicated by the white dotted box on the left panel of FIG. 3, Panel A; this average was called the M1 mean). Given the non-normal distribution of individual subject MI means (p>0.05 Kolmogorov-Smirnov test), the Kruskal-Wallis test was used to quantify the difference in coupling between diseases (FIG. 3, Panel B; p<0.01 for PD versus both other conditions). The magnitude of beta phase-broadband gamma amplitude coupling was much greater in PD subjects than in subjects with cranio-cervical dystonia or those without a movement disorder (PD 14.8±10.5, dystonia 1.3±1.3, epilepsy 2.2±2.4, mean±std; see FIG. 8, Panels A-B, FIG. 9, Panels A-B, and FIG. 11). Phase-amplitude coupling observed in dystonia and epilepsy patients was not only smaller, but occurred at lower frequencies for phase (Kruskal-Wallis, p<0.01; PD 23.1±5.5 Hz, dystonia 15.3±5.8 Hz, epilepsy 14.4±6.5 Hz, mean±std), as well as a narrower range of phase frequencies. Several computational methods are available to quantify phase-amplitude coupling. Exaggerated cortical phase-amplitude coupling in PD is invariant to choice of computational method (FIG. 10, Panels A-B).

To determine whether increased phase-amplitude coupling in PD is associated with an overall increase in beta band spectral power in PD, mean log beta power in M1 was compared between patient groups, with no difference found (Kruskal-Wallis; p>0.05; PD 7.1±1.3; dystonia 7.2±1.3, epilepsy 5.8±1.4, mean±std). Therefore, the excessive coupling in PD could not be explained on the basis of a difference in the amplitude of beta band oscillations.

Phase-amplitude coupling was compared between subject groups during performance of a simple flexion/extension elbow movement task (FIG. 3, Panel C). Although the magnitude of phase-amplitude coupling was decreased during the task compared to rest, excessive phase-amplitude coupling during the task in the parkinsonian state was evident, in comparison to dystonia and epilepsy subjects (FIG. 3, Panel D, Kruskal-Wallis p<0.01; PD 5.2±4.8; dystonia 1.3±2.3, epilepsy 0.2±0.03). All subjects were asked to make slow movements that were within the capability of those with PD, such that movement kinematics during task performance were similar across all groups (angular velocity of approximately 1 Hz in all subjects, Kruskal-Wallis p>0.05).

Example 3

Cortical Driving of Basal Ganglia Beta Oscillations

Because PD is associated with abnormal neuronal activity in the basal ganglia, phase-amplitude coupling was investigated between those two areas using the phase of STN LFPs and the amplitude of M1 LFPs, in the subjects with PD or primary dystonia. Visual inspection of this time-frequency plot revealed an increase of M1 LFP gamma power occurring at a preferred phase of the STN beta rhythm (13-30 Hz; FIG. 4, Panel A). FIG. 4, Panel B shows an example of cross structure phase-amplitude coupling observed in one PD patient (PD4). A significant coupling (z-score>4.5) between STN beta phase and the M1 gamma amplitude was found in 11 of the 15 PD patients but only 2 of the 7 dystonia patients. In PD, the strongest cortical modulation preceded the STN beta trough by ~50 ms (-58±34 ms; mean±SD, p<0.01 for difference from zero, t-test, see the black dashed line in FIG. 4, Panel A), indicating a critical role for abnormal cortical activity in maintaining excessive basal ganglia beta band synchronization.

Modulation index plots for STN-M1 coupling for all PD and dystonia patients are averaged and are shown in FIG. 4, Panel C. As shown on FIG. 4, Panel D, the phase-amplitude coupling between beta and gamma frequencies was stronger in PD than in dystonia (Kruskal-Wallis, p<0.01, PD 2.9±2.7, dystonia 0.1±0.4; FIG. 11).

The possibility that STN phase—M1 broadband gamma amplitude coupling is simply a consequence of beta band phase coherence between STN and M1 LFPs was considered. Given the strong coupling between M1 beta phase and M1 broadband gamma amplitude, any other brain structure that oscillates coherently with M1 in the beta range would have a statistical relationship between its beta phase and the M1 broadband gamma amplitude, without implying a causal connection. However, the magnitude of the coherence did not correlate with the magnitude of the STN phase-M1 amplitude coupling (mean M1 or max M1, p>0.05). In addition, there was no significant difference between the mean STN-M1 LFP beta band transformed coherence of PD and dystonia patients in spite of the fact that PD patients had much greater cross-structure phase-amplitude coupling (p>0.05). Modulation indices were computed using the phase of M1 LFPs and the amplitude of STN LFPs, which showed that coupling was generally small and reached significance only for a few combinations of phase and amplitude frequency, showing strong asymmetry in M1-STN phase-amplitude interactions.

Example 4

STN Phase-STN Amplitude Coupling

Phase-amplitude coupling was also computed using the phase and amplitude of STN LFPs. In 8 PD subjects a significant interaction between the phase of the beta rhythm and the amplitude of a relatively narrowband high frequency oscillation ("HFO") was found at >200 Hz. This pattern of STN-STN phase-amplitude coupling is distinct from beta phase-broadband gamma coupling, in that the amplitude frequency over which coupling occurs is both high and narrowband.

Example 5

Effect of Therapeutic STN DBS on Cortical Phase-Amplitude Coupling

In several PD patients, acute effects of therapeutic subthalamic deep brain stimulation were studied before, during, and after DBS (FIG. 5, Panels A-B), showing reversible suppression of exaggerated cortical phase-amplitude coupling. The exact time for wash-in and wash-out of the DBS effect varied over a time scale of minutes, precluding systematic study of the effect in all subjects, due to the time constraints of acute intraoperative recording. In each example studied, the suppression of coupling by DBS was partially washed out by 4-5 minutes post-stimulation. The wash-in of the effect was rapid in one case studied (FIG. 5, Panel A), while in a second case, the effect reached its peak after several minutes (FIG. 5, Panel B).

Example 6

High Resolution PAC Recording in M1

High resolution PAC recordings were obtained using a 28-contact grid (FIG. 12, Panel A). The locations of each of the 28 contacts of the grid were confirmed using intraoperative CT scan (FIG. 12, Panel B). The most posterior contacts covering M1 were contact 8 on the first row and contact 21 on the second row.

Phase amplitude coupling was computed for each of the 28 contacts, as described above. FIG. 13 depicts PAC observed in contacts 1-28 from FIG. 12, Panels A-B. Contact 8 (the most posterior contact covering the motor cortex M1) showed the strongest PAC. Contacts 9 and 10 (still over M1) showed lower PAC. Contacts 21 to 25 (over M1) show low PAC. No contacts show a PAC as strong as the PAC observed in contact 8. These results show that the excessive PAC associated with movement disorders is highly spatially localized, shown here by the fact that a high level of resting PAC is seen in only a few specific contacts of a 28 contact grid, and the that the strongest PAC is in a contact covering M1.

Example 7

Non-Invasive Detection of Phase-Amplitude Coupling Using Electroencephalography (EEG)

Some therapeutic mechanisms are difficult to study with an intraoperative paradigm. These include effects of oral medications, and the study of chronic versus acute DBS. The present inventors have unexpectedly discovered that cortical phase-amplitude interactions are detectable by electroencephalography (EEG) and that a comparison of (un-operated) PD subject with age matched normal subjects recapitulates the ECoG-based findings described herein that beta phase-gamma amplitude coupling is exaggerated in PD as determined by EEG (see EEG data in FIG. 21). EEG was recorded using a 32+8 channel ActiveTwo system (Biosemi instrumentation) sampled at 512 Hz. Data were referenced to a common average of all scalp EEG channels, and high pass filtered at 2 Hz. Patients were tested on two separate days, on medication or off medication for at least 12 hours, with the order counterbalanced. All data was collected during periods of alert rest.

An existing archived data set on a cohort of PD patients who do not have DBS systems, and normal controls, was investigated to validate the ability to detect PAC and reproduce our earlier finding that PD patients have exaggerated PAC; and to show reduction in PAC in the levodopa-on state (FIG. 21). PAC in PD was prominent in the contacts near M1.

FIG. 21 shows comodulogram data utilizing an existing archived data set on a cohort of PD patients who do not have DBS systems, and normal controls to validate the ability to detect PAC and reproduce earlier findings that PD patients have exaggerated PAC; and to show reduction in PAC in the levodopa-on state. Shown is average comodulogram across all subjects in each group from EEG contacts C3 and C4 (closest to M1 in each hemisphere), referenced to common average. Sixteen healthy age-matched controls (left) were compared with 15 PD patients off medication (middle) and on medication (right).

In one PD patient, the effect of chronic DBS on EEG was investigated. These data were collected using a 64+8 ActiveTwo system (Biosemi instrumentation) sampled at 1024 Hz. Data was referenced to a common average reference of all scalp EEG channels, and bandpass filtered between 2 and 280 Hz. For files recorded when DBS stimulation was on, independent component analysis was performed to eliminate the DBS artifact. It was determined that turning off therapeutic DBS (after 2 months of stimulation) resulted in a return of elevated PAC on a time course of 2-5 minutes (FIG. 22), which corresponded to the time course of return of rigidity and bradykinesia. FIG. 22 shows comodulogram data from a PD patient. The effect of chronic DBS on EEG was investigated. It was found that turning off therapeutic DBS (after 2 months of stimulation) resulted in a return of elevated PAC on a time-course of 2-5 minutes. Shown is a comodulogram during: chronic therapeutic DBS (2.2 V, monopolar STN stimulation, 180 Hz, 60 microseconds) (left); first two minutes after stopping DBS (middle); and 7-9 minutes after stopping DBS (right). Elevated PAC is more prominent over M1 (upper row) than in other areas (lower row).

It is expected that DBS will mainly affect PAC rather than EEG spectral power, that EEG will detect PAC in at least most cases, that chronic DBS will reduce PAC more than acute DBS; and that both levodopa and acute and chronic DBS will reduce cortical PAC.

Example 8

Reduction of Cortical Phase-Amplitude Coupling in Parkinson's Disease by Therapeutic Deep Brain Stimulation In the present study, the effect of basal ganglia DBS on cortical function was evaluated using cortical recording in patients undergoing DBS implantation for Parkinson's disease (PD). In the primary motor cortex of PD patients, neuronal population spiking is excessively synchronized to the phase of network oscillations, which is manifested in brain surface recordings as exaggerated coupling between the phase of the beta rhythm and the amplitude of high gamma activity. As demonstrated herein, during rest, movement preparation, and movement execution, acute therapeutic DBS reversibly reduced phase-amplitude interactions without altering the amplitude of beta activity. This occurred over a similar time course as reduction in parkinsonian motor signs. The DBS-induced changes in phase amplitude interactions were especially prominent during movement preparation. DBS of the basal ganglia may improve cortical function by alleviating excessive beta phase locking of motor cortex neurons, thereby releasing populations of neurons to engage in task performance.

Methods

Patients

Patients were recruited from two centers; the movement disorders surgery clinics at the University of California, San Francisco (UCSF) or the San Francisco Veteran's Affairs Medical Center (SFVAMC). Motor impairment was assessed preoperatively by a movement disorders neurologist (JLO) using the Unified Parkinson's Disease Rating Scale part III (UPDRS-III) in the off and on medication state. In addition, tremor and rigidity were assessed intra-operatively before each recording using UPDRS item 22 and 20, respectively. Patients included in this study had a diagnosis of idiopathic PD with bradykinesia/rigidity as predominant signs, were scheduled to undergo DBS implantation in the awake state, and gave written informed consent. Patients were excluded if they had prominent tremor during recordings or had a peak-to-peak M1 LFP amplitude of <50 microvolts at rest. Twenty patients were included. This study was in agreement with the Declaration of Helsinki and was approved by the institutional ethics committee.

Electrocorticography Strip and Lead Location

Cortical local field potentials were recorded using a 6-contact electrocorticography (ECoG) strip temporarily placed over the sensorimotor cortex. The ECoG strip was inserted under the dura through the burr hole used for the DBS lead placement and advanced in the direction of the intended target location, the arm area of motor cortex (3 cm from the midline, slightly medial to the "hand knob" Yousry et al. (1997) *Brain* 120 (Pt 1):141-157. Electrodes were composed of platinum contacts of 4 mm total diameter, 2.3 mm exposed diameter and 1 cm spacing between contacts (Ad-Tech, Racine, Wis.). Localization of the electrodes was confirmed anatomically, using either intraoperative CT merged with pre-op MRI or lateral fluoroscopy (FIG. 14, Panel A) Crowell et al. (2012) *Brain* 135:615-630. In addition, somatosensory potentials evoked by median nerve stimulation were used to select the contact used for the subsequent analyses (frequency=2 Hz, pulse width=200 μsec, pulse train length=160, amplitude 25-40 mAmp). The most posterior contact showing a negative N20 waveform was defined as the closest electrode to M1.

DBS electrodes were places in the STN as previously described. Starr et al. (2002) *Journal of Neurosurgery* 97:370-387. The STN target was identified on a T2-weighted magnetic resonance image (MRI) as a signal hypointensity, lateral to the anterior margin of the red nucleus and superior to the lateral part of the substantia nigra pars reticulata. The STN target location was typically close to 12 mm lateral, 3 mm posterior, and 4 mm inferior to the midpoint of the line connecting the anterior and posterior commissures. Final adjustments on the target coordinates were made during the surgery based on identification of movement-related single cell discharge. A DBS lead (model 3389, Medtronic, Inc., Minneapolis, Minn., USA) was then placed at these coordinates with the most ventral contact (contact 0) at the base of STN and contact 1 in the center of the motor territory of the STN. Targeting was confirmed by evaluation of stimulation induced symptom improvement and adverse effects, as well as by visualization of DBS lead location on an intra-operative CT scan computationally fused to the preoperative MRI (FIG. 14, Panel B).

Therapeutic Stimulation Parameters

STN was stimulated through the DBS lead (Medtronic model 3389) using an analog neurostimulator (Medtronic model 3625), in a bipolar configuration using parameters that typically improve symptoms. In most patients, contact 1, in the motor territory of STN was used as the active contact and the adjacent contact 2, in the dorsal border of STN, was used as the reference. Stimulation parameters were usually set at 4 Volts, 60 μs and 130 to 200 Hz. Individual subject parameters are shown in FIG. 23. In each stimulation condition, changes in the clinical symptoms were determined by assessment of contralateral limb rigidity and tremor using the UPDRS scale, item III 22 and item III 20, respectively (FIG. 23). Rigidity was used rather than bradykinesia because it responds reliably to acute DBS and can be tested rapidly without the patient's full cooperation.

FIG. 23 shows the demographic and clinical characteristics of the patients. Pre-op motor score was the Unified Parkinson's Disease Rating Scale part III on/off medication in PD. Parameters of stimulation are: contacts used; frequency, voltage and pulse width. Intra-op motor score were determined using the Unified Parkinson's Disease Rating Scale part III sub-item 22 and 20 for rigidity and tremor respectively. PD=Parkinson's disease; F=female; M=male; R=right; L=left; NA=not available.

Cortical LFP Recordings

Cortical LFPs were recorded in a bipolar configuration referencing the five most posterior contacts (contacts 1-5) to the most anterior one (contact 6) and using a needle electrode in the scalp as the ground. Signals were bandpass filtered 1-500 Hz, amplified×7000. LFPs were recorded using the Alpha Omega Microguide Pro (Alpha Omega, Inc, Nazareth, Israel) (15 patients) or the customized clinical recording systems, the Guideline 4000 system (FHC Inc, Bowdoin, Me.) (5 patients). LFPs were recorded at a sampling rate of minimum 1000 Hz and up to 3000 Hz. All antiparkinsonian medications were stopped 12 hours before the start of surgery.

Behavioral Paradigms

Two behavioral states were used. In all subjects, cortical LFPs were recorded before, during and after acute STN stimulation while patient relaxing, eyes open, fixating a point approximately 1 meter away, for at least 30 seconds (rest). 12 of these patients performed an arm movement task in the same conditions of stimulation. The task was designed to study the effect of DBS not only on movement execution but also on its preparation (FIG. 14, Panel C). Each trial starts with a 'hold' period of 5-7 s during which the subject was asked to rest his hand on his lap, while maintaining gaze on a central red dot. Then, the 'target', a blue dot, occurs at the upper or lower edge of the screen. The position of the target was randomly chosen as either the upper and lower edge of the screen. A change of color from red to green ('go' signal) instructs the patient to touch with the index finger the target that will then step vertically form one position to the other (usually 5 steps). The duration between the target onset and the go signal was 3-5 s depending on patient ability. Patients performed ten to twenty trials in both stimulation conditions. The task was performed on a mobile device (iPad, Apple computers). This task allow us to distinguish 3 phases: The hold phase, the movement preparation phase and the movement phase. Movement kinematics were measured both by electromyography of extensor carpi radialis, flexor carpi radialis and biceps brachii (bandpass filter 1-1000 Hz, amplification×7000, sampling rate of 1 to 3 KHz) and/or accelerometry. FIG. 14, Panel D represents the typical timeline for stimulation and recording.

Signal Processing and Analysis

In order to obtain a better spatial localization and reduced noise, LFPs recorded from each contact were re-referenced to its posterior adjacent contact (C1-C2, C2-C3 . . . ). Ambient noise (60 Hz and harmonics) was rejected off line using a notch filter. Given the distance between stimulation and recording sites and/or the bipolar montage used to analyze the data, the stimulation artifact was small relative to the cortical signal, in most recordings (FIG. 15). Stimulation artifact was filtered out using a notch filter (Butterworth filter, bandwidth=4). LFPs recorded with a frequency sampling greater than 1000 Hz were down sampled to 1000 Hz. For data recorded at rest, the first 30 s of data without obvious electrical noise or movement were selected for the analyses. For data recorded during the task, trials during which subject initiated movement before the go signal were excluded from the analyses. In order to study the effect of task phase, time series data were separated into hold, preparation and movement phases, each movement phase was divided into 1 second segments, excluding the segment at the transition points. Analyses were done on each 1 sec segment then averaged for all segments within a specific task phase. All analyses were performed using Matlab 7.10 software (Mathworks).

In the resting condition, Power spectral density (PSD) was calculated with the Welch periodogram method (Matlab function pwelch) using a fast Fourier transform of 512 points (frequency resolution of 1.95 Hz), and 50% overlap, using a Hanning window to reduce edge effects. PSD was computed in the three conditions of stimulation and was transformed in logarithm scale and used for all statistical comparisons to allow for use of parametric tests. Three variables were extracted from the log PSD; the "beta peak" defined as the maximum value between 13 and 30 Hz; the "beta peak frequency" defined as the frequency at which the "beta peak" occurred and "log beta power" defined as the average of the log PSD across the beta band (13-30 Hz).

In the task, cortical changes related to movement preparation and movement initiation were studied using a time frequency analysis. Cortical power spectral density was computed using the short time Fourier transform ('spectrogram'; MATLAB function) with a 512-point window and 50 sample (50 ms) frame advance. PSD were aligned on either on the 'target' occurrence, corresponding to the end of the hold phase, or on the movement onset. Each frequency of the PSD was then normalized to the baseline defined as the PSD averaged across 1 s prior to target onset. Four variables were then computed: 'β changes prep' and 'γ changes prep' were determined by averaging the time spectrograms across a period from 1 s before to the 'go' signal in the beta band (13-30 Hz) and broadband gamma (50-200), respectively. 'β changes mvt' and 'γ changes mvt' were determined by averaging the time spectrograms across 1 s at movement onset in the beta band (13-30 Hz) and broadband gamma (50-200), respectively, Each variable was expressed as the percentage of changes from baseline.

Phase-amplitude coupling indices were quantified using a method previously described (Tort et al., (2008) *Proc Natl Acids Sci* 105:20517-20522). First, cortical LFPs were bandpass filtered at low (from 4 to 50 Hz in 2 Hz steps with a 2 Hz bandwidth, without overlap) and high frequency (from 50 to 200 Hz in 4 Hz steps with a 4 Hz bandwidth, without overlap) using a FIR1 filter (eeglab). Second, the instantaneous phase and the instantaneous amplitude were extracted from the low and the high frequency filtered signal, respectively, after applying the Hilbert transform. The instantaneous phase was divided into bins of 20° and a distribution of the instantaneous amplitude envelope was computed for each bin. The phase-amplitude coupling was then determined by computing the entropy values of this distribution and normalizing by the maximum entropy value. Coupling was computed for multiple frequencies for phase and amplitude represented on a modulation index plot (FIG. 16, Panel A). In addition, for each frequency pair, the phase of the coupling ("preferred phase") was calculated by determining the phase at which the instantaneous amplitude was maximal. For each patient and each stimulation condition, the overall magnitude (PAC mean) of beta-broadband gamma coupling was determined by averaging the coupling between phases extracted from the 13-30 Hz band and the amplitude extracted from the 50-200 Hz band. The 'mean preferred phase' was computed by averaging the 'preferred phase' computed frequency for phase between 13-30 Hz band and frequency for amplitude between 50-200 Hz band (circ_mean.m from the circular statistics toolbox). In addition, the frequencies involved in the maximal coupling (PAC freq phase and PAC freq amp) were determined.

Between Group Statistical Analysis

Statistical analyses were performed in SPSS and Matlab. Statistical analyses were performed using paired non parametric tests given the non-normal distribution of most variables studied (Ranktest, Ranksign test, Friedman test and spearman correlation).

Results

Cortical LFPs were recorded in a total of 20 PD patients before, during and after STN stimulation at rest. Twelve of the 20 were also tested while performing the arm movement task (FIG. 14, Panel C). Clinical characteristics are provided in FIG. 23. Representative examples of cortical LFPs recorded from the motor cortex of a PD patient (PD 5) before, during and after STN stimulation, and their respective log power spectral densities are shown in FIG. 15. The stimulation artifact was small relative to the cortical signal.

DBS Reduces Resting State PAC and Rigidity

FIG. 16, Panel A shows PAC before, during and after STN stimulation for a representative patient (PD1). A strong interaction was observed between the phase of beta oscillations and the amplitude of gamma activity over a broad spectral range of 50-150 Hz, often referred to as "broadband gamma" (left panel). A similar pattern of PAC was observed in each PD patient before stimulation. PAC was strongly reduced during STN stimulation (middle panel) and increased after the stimulation was turned off (right panel). In order to quantify the effect of DBS on this interaction, the modulation index computed for each patient in each condition of stimulation, was averaged across the all beta band and the broadband gamma (frequency for phase 13-30 Hz; frequency for amplitude 50-200 Hz) as shown by the white dotted box FIG. 16, Panel A (left panel). This average coupling (PAC mean) was computed for each patient, in each condition of stimulation and used for statistical group comparison, using nonparametric tests given its non-normal distribution (p<0.001 Kolmogorov-Smirnov test, FIG. 24). Group analysis showed a reduction of phase-amplitude coupling during DBS (FIG. 16, Panel B, left panel; Friedman test, p=0.0017; before DBS, 0.0015±0.0023; during DBS, 0.0009±0.0015; after DBS, 0.0013±0.002) and a trend for return to baseline PAC within five min after DBS (FIG. 16, Panel B, right panel; ranksign test, p=0.07). Boxplots of phase-amplitude coupling computed in each condition of stimulation are shown in FIG. 16, Panel C. Acute DBS also reduced parkinsonian motor signs as reflected in the rigidity score (UPDRS item 22), and similar to the effect on PAC, there was an incomplete washout of the clinical effect of stimulation on rigidity (FIG. 16, Panel D). A significant correlation between PAC mean and the intra-operative rigidity score was observed before DBS (spearman correlation, p=0.034; r=0.50) and after DBS (spearman correlation; p=0.017; r=0.65). We did not find a significant correlation between rigidity reduction and DBS induced change in PAC, likely due to the low range of rigidity changes (rigidity changes=0-2).

In order to better characterize the effect of DBS on phase-amplitude coupling, we also determined the preferred phase of the coupling (PAC preferred phase; before DBS 0.74±1.6; during DBS 0.63±1.9; after DBS 1.00±1.55 Hz), the frequencies involved in this maximal coupling (PAC phase freq; before DBS 17.2±4.8; during DBS 16.8±4.6; after DBS 16.8±4.8 Hz and PAC amp freq; before DBS 96.3±34.9; during DBS 94.3±35.4; after DBS 94.0±38.3 Hz). None of these variables were affected by DBS (Friedman test, p>0.05, FIG. 24) suggesting that DBS reduces the magnitude of phase-amplitude coupling without changing the preferred phase or frequencies involved in such coupling.

FIG. 24 shows the effect of DBS at rest. PAC β=Phase-amplitude coupling average across beta (13-30 Hz) and gamma (50-200 Hz) bands; PAC phase=preferred phase; PAC max freq=frequency at which the maximal coupling occurred; Mean psd β=average of the log psd across the beta band (13-30 HZ); Max psd=maximum of the log psd; Max psd freq=frequency corresponding to the maximum of the log psd; Mean psd Y=average of the log psd across the broadband gamma (50-200 HZ). Asterisks indicate significant comparison after correction for multiple comparisons.

DBS does not Change Beta or Gamma Power Test

In order to assure that the change in resting state phase-amplitude coupling was not due to a change in beta or gamma power, power spectral density was computed for each patient and in each condition of stimulation, focusing on these two frequency bands. A peak of oscillatory activity in the alpha-beta band was observed in the motor cortex of all patients before, during and after stimulation (FIG. 15, Panel B). Several parameters were extracted in order to better characterize this beta band spectral peak and its modulation by DBS (FIG. 25). We found that the frequency of the beta peak (beta peak freq; before DBS 19.0±3.8 Hz; during DBS 20.2±3.12 Hz; after DBS 18.8±4.3 Hz), its power (beta peak; before DBS 0.96±0.4; during DBS 0.98±0.4; after DBS 0.91±0.3 Hz) and its average over the all band (log beta beta; before DBS 1.54±0.8; during DBS 1.48±0.7; after DBS 1.49±0.8) were similar irrespective of the stimulation condition (FIG. 17, Panel A, Friedman test, p>0.05). Broadband gamma is thought to reflect underlying asynchronized spiking activity and is therefore not characterized by a peak in the power spectral density. As shown on FIG. 17, Panel B, the average log PSD over the gamma band was not affected by DBS. These results suggest that the reduction of coupling during STN stimulation is not due to a change in beta or gamma power but rather to a decrease in their interaction.

FIG. 25 shows the effect of DBS on phase-amplitude coupling during the task. PAC β hold=phase-amplitude coupling computed during the hold phase of the task and averaged across the beta (13-30 Hz) and gamma (50-200 Hz); PAC β prep=phase-amplitude coupling computed during movement preparation; PAC β mvt=phase-amplitude coupling computed during movement execution. Asterisks indicate significant comparison after correction for multiple comparisons.

Movement and DBS Reduce PAC During Task Performance

Given that therapeutic intervention could have different effects on different aspects of movement, cortical synchronization was also studied while patients performed a reaching movement task allowing us to distinguish three phases; the 'hold' phase during which the patient resting the hand on a button while looking at a fixation point on the screen, the 'preparation' phase during which a target appeared on the screen, and a 'movement' phase during which patient touching the target on screen (FIG. 14, Panel C). Patients performed ten to twenty trials in each of three DBS conditions: pre-DBS, during DBS, and post DBS. Trials during which movement was initiated before the occurrence of the 'go' signal were excluded from the analyses. Examples of cortical LFPs recorded in M1 of PD1 and the corresponding accelerometry trace are shown in FIG. 18, Panel A. The effect of task phases and stimulation conditions on PAC in an individual patient is shown on FIG. 18, Panel B (PD7). PAC was reduced from hold (left panel) to preparation phase (middle panel) and was even further reduced during movement execution (right panel). In all three phases, STN DBS induced an additional reduction of phase-amplitude coupling (middle raw) that partly returned to baseline after stimulation was stopped (lower raw). Group analyses are summarized in FIG. 25. A significant reduction of phase-amplitude coupling by task phases was found (FIG. 19; Friedman test p<0.001). STN DBS significantly reduced this coupling in all three phases but especially during movement preparation (Friedman test p<0.001; After DBS, phase-amplitude coupling increased toward values observed before STN stimulation (Friedman test p<0.001); Although DBS reduced the PD symptoms formally tested rigidity and tremor (when present), it did not in general improve task performance, such as reaction time (Friedman test, p>0.05). However, this is not surprising since, in order to avoid anticipatory responses, patients were instructed to move only after the occurrence of the go signal and not to move as fast as possible after its occurrence. Therefore our paradigm did not specifically test reaction time.

DBS does not Change Beta or Gamma Power During Movement Planning or Execution

A strong decrease in the beta band during both movement preparation and movement execution was observed (FIG. 20, Panel A) and has been observed in persons without movement disorders. Movement related beta changes were not significantly affected by the condition of stimulation (FIG. 26; Friedman test; p>0.05). Another normal feature of movement related change in the sensorimotor cortex is an increase in gamma band that is thought to reflect local cortical activation (Crone et al., 1998a, Miller et al., 2012). Here, we found a significant increase in gamma activity at movement onset that was similar in all three stimulation conditions (FIG. 20, Panel B; FIG. 27; Friedman test; p>0.05). These results suggest that DBS does not modulate beta or gamma activity but decreases the interaction between both frequency bands.

FIG. 26 shows the effect of DBS and behavioral state on log 0. Mean psd β hold=time PSD computed during the last second of the hold phase of the task and averaged across the broadband (13-30 Hz); β changes prep=time PSD averaged from 1 s before to the "go" signal, across the β band (13-30 Hz); β changes mvt=time PSD averaged across the first second of movement. Asterisks indicate significant comparison after correction for multiple comparisons.

FIG. 27 shows the effect of DBS and behavioral state on log Y. Mean psd Y hold=time PSD computed during the last second of the hold phase of the task and averaged across the broadband (50-200 Hz); Y changes prep=time PSD averaged from 1 s before to the 'go' signal, across the Y band (50-200 Hz); Y changes mvt=time PSD averaged across the first second of movement.

Discussion

The effect of STN stimulation on the function of the primary motor cortex was investigated in PD patients undergoing physiologically guided DBS electrode placement in the awake state. It was found that interactions between the phase of the beta rhythm and the amplitude of broadband gamma activity were decreased during acute therapeutic DBS both at rest and during a task, especially in the preparation phase of the task. Further, it was found that DBS restores movement-related increases in cortical gamma activity, which is a fundamental feature of normal movement that may be impaired in PD. Our results underscore the importance of exaggerated PAC as a mechanism relevant to the expression of PD symptoms, and suggest the incorporation of cortical PAC measures into the design of closed-loop DBS paradigms.

Attenuation of Phase-Amplitude Coupling

PAC is considered to be an important mechanism for the coordination between anatomically dispersed neuronal cell assemblies, both in motor function and in cognitive functions such as memory, learning and attention. The results of the present study provide evidence for an important role of cortical PAC in the pathophysiology of PD since a therapy that reversibly improves motor signs, also reversibly reduces exaggerated PAC, with a similar time course.

Strong coupling between beta oscillations and very high frequency rhythms (>250 Hz) have been shown in basal ganglia field potential recordings. While cortical PAC involved broadband gamma (50-200 Hz), thought to represent the summed asynchronous spiking activity, the coupling observed in STN involved narrow band rhythms (250-350 Hz) of less clear origin.

Role of DBS in Movement-Related PAC Changes

In the sensorimotor cortex in the normal state, beta-broadband gamma PAC is strongly reduced during both movement preparation and execution. The high PAC state may suppress cortical information processing at rest and its cessation before movement onset may induce a shift to an active processing state. Our results showed that, although PD patients could accomplish this transition, it was facilitated by therapeutic DBS, which reduced PAC at each phase of movement. Elevated PAC in the resting state and during movement preparation may be associated with akinesia and rigidity, while elevated PAC during movement execution may be associated with bradykinesia. STN DBS improves these symptoms by reducing the excessive PAC in all conditions.

DBS does not Reduce Cortical Beta Power

A current working hypothesis for the mechanism of DBS is suppression of basal ganglia oscillatory activity especially the beta band (13-30 Hz). This hypothesis is derived largely from recordings of local field potentials in the STN of PD patients that have shown a prominent beta power that is reduced by therapeutic medications and by therapeutic DBS in a manner that correlates with symptom improvement. However, to date, there is no evidence of increased beta power in PD patients off medication compared to non parkinsonian subjects or PD patients on medication. In one prior paper using ECoG in PD, Whitmer et al. (2012) found an attenuation of beta power during acute STN DBS in the motor cortex of two of the three patients tested. Here, with anatomically similar electrode placement in a much larger sample size, we found that DBS in individual subjects produced modest decreases or increases in beta power without consistent change in grouped data. Our findings indicate that the amplitude of beta oscillations may play a less important role in the pathophysiology of PD and in the mechanism of DBS, at least at the cortical level. Rather, the entrainment of population spiking to the beta rhythm, as measured by beta-broadband gamma coupling, may be a better biomarker of the parkinsonian state and of the effectiveness of therapeutic intervention.

Entrainment of Subcortical Axonal Firing and Reduction of Cortical PAC

DBS is thought to partially entrain action potential firing in axons in close proximity to the stimulating electrode, which may be either afferent or efferent with respect to the stimulated nucleus. Axonal antidromic spikes evoked by STN DBS strongly affect the firing probability of cortical neurons, inducing short periods of inhibition and excitation. This DBS-generated pattern of firing probability, if present at the optimal frequency, probably serves to decouple the strong dependence of spike firing on beta phase in M1.

Improved Therapy

The reduction in cortical PAC by DBS implies that PAC could be used as a control signal for "close-loop" DBS devices. Such "smart" DBS devices may record cortical activity, quickly compute phase-amplitude coupling and determine computationally how to stimulate subcortical structures in a manner that best minimizes abnormal network activity. Development of closed-loop DBS devices will have an important impact in the treatment of movement disorders by overcoming the main limits of the current therapy such as the labor-intensive programming based on frequent symptom assessment by clinicians, stimulation induced adverse effects, the habituation (less efficacy over time), and short battery life. Two approaches to the development of closed loop stimulation devices have been proposed, one utilizing cortical single unit activity and another utilizing STN LFP beta oscillations. Implementation of these strategies in a fully implantable closed loop system is hampered by the risk and signal stability of cortical unit recording for the former approach, and by the low signal to noise ratio and high susceptibility to stimulation artifact for the latter. The present study provides a strategy to overcome these issues by measuring the neuronal synchronization (using phase-amplitude coupling) at the cortical level. This approach may use high amplitude signals with minimal stimulation artifact, and a recording electrode that does not penetrate brain tissue. This strategy may be generalized to other neurologic or psychiatric diseases.

Conclusion

In Parkinson's disease, acute therapeutic DBS acts on the cortex by reducing the excessive coupling between beta oscillations and broadband gamma activity not only at rest but also during movement preparation and execution. The results of the present study indicate that phase-amplitude coupling is a biomarker of the parkinsonian state that could be used to improve the DBS therapy by developing adaptive DBS devices based on PAC.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for reducing clinical presentations of a neurological movement disorder in a subject, the method comprising:
   (i) administering a first deep brain stimulus train to the subject;
   (ii) measuring cortical local field potentials (LFPs) from a surface of the subject's primary motor cortex using at least one electrode, wherein the at least one electrode is located at a position corresponding to an arm area of primary motor cortex M1;
   (iii) calculating, with a processor, a modulation index for synchronization of brain rhythms in the LFPs, wherein the synchronization of brain rhythms in the LFPs comprises synchronization of phase of beta rhythm and amplitude of gamma activity; and
   (iv) administering a second deep brain stimulus train to the subject when the calculated modulation index is outside of a predefined threshold range;
   wherein steps (i)-(iv) are continued in a manner effective to reduce the clinical presentations of the neurological movement disorder.

2. The method according to claim 1, wherein at least one parameter of the second deep brain stimulus train is different relative to the first deep brain stimulus train.

3. The method according to claim 2, wherein the at least one parameter is selected from the group consisting of contact choice, amplitude, and frequency.

4. The method according to claim 1, further comprising changing, with the processor, at least one parameter of the first deep brain stimulus train prior to administering the second deep brain stimulus train if the calculated modulation index is outside of the predefined threshold range.

5. The method according to claim 1, wherein administering the first or second deep brain stimulus train to the subject comprises stimulating one or more structures in the subject's thalamus, basal ganglia, or both.

6. The method according to claim 5, wherein administering the first or second deep brain stimulus train to the subject comprises stimulating the subject's subthalamic nucleus (STN) or globus pallidus.

7. The method according to claim 5, wherein the stimulation is administered using a stimulation electrode array.

8. The method according to claim 1, further comprising placing a stimulation electrode array in the subject's brain to administer deep brain stimulation.

9. The method according to claim 8, further comprising placing the stimulation electrode array in one or more structures in the subject's thalamus, basal ganglia, or both.

10. The method according to claim 9, further comprising placing the stimulation electrode array in the subject's subthalamic nucleus (STN) or globus pallidus.

11. The method according to claim 1, wherein the predefined threshold range is tailored for the subject.

12. The method according to claim 1, further comprising placing the at least one electrode on the surface of the subject's brain, wherein the at least one electrode is placed at a position corresponding to an arm area of primary motor cortex M1.

13. The method according to claim 12, wherein the electrode is a non-brain-penetrating electrode.

14. The method according to claim 1, further comprising digitizing the LFPs at a sampling rate of about 400 to 2000 samples per second prior to calculating the modulation index.

15. The method according to claim 1, further comprising digitizing the LFPs at a sampling rate of about 400 to 800 samples per second prior to calculating the modulation index.

16. The method according to claim 1, further comprising filtering out the LFPs that are not in a frequency range of about 15 Hz to about 30 Hz, thereby generating a set of LFPs that comprise a frequency range of about 15 Hz to about 30 Hz prior to calculating the modulation index.

17. The method according to claim 1, further comprising filtering out the LFPs that are not in an amplitude range of about 50 Hz to about 200 Hz, thereby generating a set of LFPs that comprise an amplitude range of about 50 Hz to about 200 Hz prior to calculating the modulation index.

18. The method according to claim 1, wherein calculating the modulation index comprises calculating a Kullback-Liebler-based modulation index.

19. The method according to claim 1, wherein calculating the modulation index comprises calculating a mean vector length modulation index.

20. The method according to claim 1, wherein calculating the modulation index comprises applying a phase-amplitude coupling palette method.

21. The method according to claim 1, wherein calculating the modulation index comprises applying a linear regression.

22. The method according to claim 1, further comprising administering an effective amount of a pharmacological agent to the subject.

23. The method according to claim 22, wherein the pharmacological agent is selected from the group consisting of levodopa, carbidopa, catechol O-methyltransferase inhibitors, monoamine oxidase inhibitors, dopamine agonists, anticholinergics, catecholamines, baclofen, benzodiazepines, tetrabenezine, diazepam, clonazepam, and lorazepam.

24. The method according to claim 22, wherein the administering comprises infusion.

25. The method according to claims 22, wherein the pharmacological agent is administered to the subject if the calculated modulation index is outside of the predefined threshold range, and wherein administration of the pharmacological agent is controlled by the processor.

26. The method according to claim 25, wherein the processor changes at least one parameter of the administration of the pharmacological agent if the calculated modulation index is outside of the predefined threshold range.

27. The method according to claim 1, wherein the neurological movement disorder comprises Parkinson's disease.

28. The method according to claim 27, wherein the subject has been diagnosed with Parkinson's disease.

29. The method according to claim 1, wherein the neurological movement disorder comprises dystonia.

30. The method according to claim 29, wherein the subject has been diagnosed with dystonia.

31. The method according to claim 1, wherein the subject is human.

32. The method according to claim 1, wherein the measuring cortical LFPs is by electrocorticography (ECoG).

33. The method according to claim 1, wherein the measuring cortical LFPs is by electroencephalography (EEG).

34. The method according to claim 1, wherein the cortical LFPs are measured during movement preparation.

35. The method according to claim 1, wherein the cortical LFPs are measured during movement execution.

36. The method according to claim 1, wherein the cortical LFPs are measured during rest.

* * * * *